US011718853B2

(12) United States Patent
Levitt, Jr.

(10) Patent No.: US 11,718,853 B2
(45) Date of Patent: *Aug. 8, 2023

(54) LOCALIZED THERAPY OF LOWER AIRWAYS INFLAMMATORY DISORDERS WITH PROINFLAMMATORY CYTOKINE INHIBITORS

(71) Applicant: Onspira Therapeutics, Inc., Wayne, PA (US)

(72) Inventor: Roy C Levitt, Jr., Miami Beach, FL (US)

(73) Assignee: ONSPIRA THERAPEUTICS, INC., Wayne, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/366,835

(22) Filed: Jul. 2, 2021

(65) Prior Publication Data
US 2021/0395748 A1 Dec. 23, 2021

Related U.S. Application Data

(63) Continuation of application No. 16/714,948, filed on Dec. 16, 2019, now Pat. No. 11,091,763, which is a continuation of application No. 14/605,545, filed on Jan. 26, 2015, now Pat. No. 10,550,389, which is a continuation of application No. 12/377,027, filed as application No. PCT/US2007/017800 on Aug. 10, 2007, now Pat. No. 8,940,683.

(60) Provisional application No. 60/907,028, filed on Mar. 16, 2007, provisional application No. 60/878,385, filed on Jan. 4, 2007, provisional application No. 60/836,760, filed on Aug. 10, 2006.

(51) Int. Cl.
| | | |
|---|---|---|
| A61K 9/00 | (2006.01) | |
| C12N 15/113 | (2010.01) | |
| A61K 38/20 | (2006.01) | |
| A61K 31/70 | (2006.01) | |
| C07K 14/715 | (2006.01) | |
| A61P 11/08 | (2006.01) | |
| A61K 31/7088 | (2006.01) | |
| A61K 31/713 | (2006.01) | |
| A61K 38/17 | (2006.01) | |
| A61K 39/395 | (2006.01) | |
| A61K 45/06 | (2006.01) | |

(52) U.S. Cl.
CPC .......... *C12N 15/1136* (2013.01); *A61K 9/007* (2013.01); *A61K 9/008* (2013.01); *A61K 9/0075* (2013.01); *A61K 9/0078* (2013.01); *A61K 31/70* (2013.01); *A61K 31/7088* (2013.01); *A61K 31/713* (2013.01); *A61K 38/1793* (2013.01); *A61K 38/20* (2013.01); *A61K 38/2006* (2013.01); *A61K 39/3955* (2013.01); *A61K 45/06* (2013.01); *A61P 11/08* (2018.01); *C07K 14/7155* (2013.01); *C12N 15/113* (2013.01); *C07K 2319/30* (2013.01); *C12N 2310/11* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 4,668,218 | A | 5/1987 | Virtanen |
| 5,116,964 | A | 5/1992 | Capon et al. |
| 5,136,021 | A | 8/1992 | Dembinski et al. |
| 5,147,638 | A | 9/1992 | Esmon et al. |
| 5,149,780 | A | 9/1992 | Plow et al. |
| 5,196,511 | A | 3/1993 | Plow et al. |
| 5,204,445 | A | 4/1993 | Plow et al. |
| 5,223,395 | A | 6/1993 | Gero |
| 5,225,538 | A | 7/1993 | Capon et al. |
| 5,231,024 | A | 7/1993 | Moeller et al. |
| 5,262,520 | A | 11/1993 | Plow et al. |
| 5,306,620 | A | 4/1994 | Ginsberg et al. |

(Continued)

FOREIGN PATENT DOCUMENTS

| | | |
|---|---|---|
| EP | 0218868 A2 | 4/1987 |
| EP | 237507 A1 | 9/1987 |

(Continued)

OTHER PUBLICATIONS

Balbi et al., (2000) Inhaled corticosteroids in stable COPD patients: do they have effects on cells and molecular mediators of airway inflammation? Chest, 117:1633-1637.

Bolon et al. (2003) Impact of Systemic Antagonism of Interleukin-1 (IL-1) or Tumor Necrosis Factor (TNF) on Arthritis Induced by Intra-Articular Instillation of IL-1 beta, TNF-alpha, or Lipopolysaccharide (LPS), Annals of Rheumatic Diseases, vol. 62, Suppl. 1, p. 123.

De Boer (2005) Perspectives for Cytokine Antagonist Therapy in COPD, Drug Discovery Today, 10:93-106.

Efthimiou et al. (2005) Role of Biological Agents in Immune-Mediated Inflammatory Diseases, South Med. J., 98:192-204.

European Search Report and Search Opinion, dated May 27, 2020, received in related European Patent Application No. 19204691.0 (16 total pages).

(Continued)

*Primary Examiner* — Sean Mcgarry
(74) *Attorney, Agent, or Firm* — Wilmer Cutler Pickering Hale and Dorr LLP

(57) ABSTRACT

The present invention is drawn to methods and compositions for treating inflammatory disorders of the lower airways, comprising administering an effective amount of an agent, which modulates the expression and/or activity of a proinflammatory cytokine or fragment thereof, preferably in a human. The proinflammatory cytokine contemplated by the invention includes IL-1, IL-6, IL-8 and TNF-alpha. The present invention describes a kit comprising a delivery device and a pharmaceutical composition for administration of the agent. The pharmaceutical composition includes at least one proinflammatory cytokine inhibitor, optionally one or more additional active ingredients, and at least one pharmaceutically active carrier. The delivery device further comprises a nebulizer, an inhaler, a powder dispenser, an intrapulmonary aerosolizer and a sub-miniature aerosolizer.

26 Claims, No Drawings

(56) References Cited

U.S. PATENT DOCUMENTS

| | | | |
|---|---|---|---|
| 5,334,380 | A | 8/1994 | Kilbourn et al. |
| 5,360,716 | A | 11/1994 | Ohmoto et al. |
| 5,404,871 | A | 4/1995 | Goodman et al. |
| 5,426,181 | A | 6/1995 | Lee et al. |
| 5,436,154 | A | 7/1995 | Barbanti et al. |
| 5,447,851 | A | 9/1995 | Beutler et al. |
| 5,458,135 | A | 10/1995 | Patton et al. |
| 5,478,725 | A | 12/1995 | Lessey |
| 5,498,694 | A | 3/1996 | Ruoslahti |
| 5,513,630 | A | 5/1996 | Century |
| 5,523,209 | A | 6/1996 | Ginsberg et al. |
| 5,542,412 | A | 8/1996 | Century |
| 5,570,686 | A | 11/1996 | Century |
| 5,578,704 | A | 11/1996 | Kim et al. |
| 5,579,578 | A | 12/1996 | Ashley, Jr. |
| 5,579,758 | A | 12/1996 | Century |
| 5,589,570 | A | 12/1996 | Tamura et al. |
| 5,594,987 | A | 1/1997 | Century |
| 5,606,789 | A | 3/1997 | Century |
| 5,610,279 | A | 3/1997 | Brockhaus et al. |
| 5,644,034 | A | 7/1997 | Rathjen et al. |
| 5,652,109 | A | 7/1997 | Kim et al. |
| 5,652,110 | A | 7/1997 | Kim et al. |
| 5,656,272 | A | 8/1997 | Le et al. |
| 5,658,746 | A | 8/1997 | Coan et al. |
| 5,693,612 | A | 12/1997 | Jonczyk et al. |
| 5,698,195 | A | 12/1997 | Le et al. |
| 5,705,481 | A | 1/1998 | Jonczyk et al. |
| 5,736,138 | A | 4/1998 | Pfizenmaier et al. |
| 5,741,488 | A | 4/1998 | Feldman et al. |
| 5,753,230 | A | 5/1998 | Brooks et al. |
| 5,767,071 | A | 6/1998 | Palladino et al. |
| 5,770,565 | A | 6/1998 | Cheng et al. |
| 5,780,426 | A | 7/1998 | Palladino et al. |
| 5,808,029 | A | 9/1998 | Brockhaus et al. |
| 5,817,457 | A | 10/1998 | Bird et al. |
| 5,830,678 | A | 11/1998 | Carter |
| 5,849,692 | A | 12/1998 | Jonczyk et al. |
| 5,863,769 | A | 1/1999 | Young |
| 5,908,839 | A | 6/1999 | Levitt et al. |
| 5,919,452 | A | 7/1999 | Le et al. |
| 5,955,572 | A | 9/1999 | Ruoslahti et al. |
| 5,958,412 | A | 9/1999 | Welt et al. |
| 5,959,087 | A | 9/1999 | Rathjen et al. |
| 5,968,741 | A | 10/1999 | Plevy et al. |
| 5,985,278 | A | 11/1999 | Mitjans et al. |
| 5,994,510 | A | 11/1999 | Adair et al. |
| 6,016,800 | A | 1/2000 | Century |
| 6,029,657 | A | 2/2000 | Century |
| 6,036,978 | A | 3/2000 | Gombotz et al. |
| 6,037,149 | A | 3/2000 | Levitt et al. |
| 6,041,775 | A | 3/2000 | Century |
| 6,048,861 | A | 4/2000 | Askew et al. |
| 6,090,944 | A | 7/2000 | Hutchinson |
| 6,096,707 | A | 8/2000 | Heino et al. |
| 6,114,517 | A | 9/2000 | Monia et al. |
| 6,130,231 | A | 10/2000 | Wityak et al. |
| 6,153,628 | A | 11/2000 | Jin et al. |
| 6,160,099 | A | 12/2000 | Jonak et al. |
| 6,171,588 | B1 | 1/2001 | Carron et al. |
| 6,171,787 | B1 | 1/2001 | Wiley |
| 6,294,655 | B1 | 9/2001 | Ford et al. |
| 6,365,726 | B1 | 4/2002 | Ballinger et al. |
| 6,576,434 | B1 | 6/2003 | Holroyd et al. |
| 6,737,427 | B2 | 5/2004 | Zhou et al. |
| 6,746,839 | B1 | 6/2004 | Duff et al. |
| 7,507,745 | B2 | 3/2009 | Meade et al. |
| 7,695,717 | B2 | 4/2010 | Masat et al. |
| 7,709,461 | B2 | 5/2010 | Liu et al. |
| 8,008,350 | B2 | 8/2011 | Luker et al. |
| 8,048,910 | B2 | 11/2011 | Maus et al. |
| 8,637,469 | B2 | 1/2014 | Levitt |
| 8,680,241 | B2 | 3/2014 | Naparstek et al. |
| 8,940,683 | B2 | 1/2015 | Levitt |
| 10,550,389 | B2 | 2/2020 | Levitt, Jr. |
| 11,091,763 | B2 | 8/2021 | Levitt |
| 2002/0128179 | A1 | 9/2002 | Tacon et al. |
| 2002/0156009 | A1 | 10/2002 | Ballinger et al. |
| 2003/0049256 | A1 | 3/2003 | Tobinick |
| 2003/0099650 | A1 | 5/2003 | Ho et al. |
| 2003/0143603 | A1 | 7/2003 | Giles-Komar et al. |
| 2004/0009149 | A1 | 1/2004 | Altman et al. |
| 2004/0010119 | A1 | 1/2004 | Guo et al. |
| 2006/0122105 | A1 | 6/2006 | Strom et al. |
| 2006/0292224 | A1 | 12/2006 | Moore et al. |
| 2007/0021360 | A1 | 1/2007 | Nyce et al. |
| 2007/0218063 | A1 | 9/2007 | Skurkovich et al. |
| 2008/0268044 | A1 | 10/2008 | Appleby et al. |
| 2008/0311111 | A1 | 12/2008 | Drew et al. |
| 2009/0191217 | A1 | 7/2009 | de Wildt et al. |
| 2010/0129316 | A1 | 5/2010 | Levitt |
| 2014/0311482 | A1 | 10/2014 | Levitt, Jr. |

FOREIGN PATENT DOCUMENTS

| | | |
|---|---|---|
| EP | 0288088 A2 | 10/1988 |
| JP | 2004-511515 A | 4/2004 |
| WO | WO-91/02078 A1 | 2/1991 |
| WO | WO-92/07076 A1 | 4/1992 |
| WO | WO-94/06498 A1 | 3/1994 |
| WO | WO-94/08552 A2 | 4/1994 |
| WO | WO-94/16970 A1 | 8/1994 |
| WO | WO-95/22543 A1 | 8/1995 |
| WO | WO-97/22376 A1 | 6/1997 |
| WO | WO-97/25086 A2 | 7/1997 |
| WO | WO-98/33919 A2 | 8/1998 |
| WO | WO-98/35888 A1 | 8/1998 |
| WO | WO-98/40488 A1 | 9/1998 |
| WO | WO-98/46264 A1 | 10/1998 |
| WO | WO-99/27086 A1 | 6/1999 |
| WO | WO-00/31248 A1 | 6/2000 |
| WO | WO-00/62736 A2 | 10/2000 |
| WO | WO-00/78815 A1 | 12/2000 |
| WO | WO-01/02571 A2 | 1/2001 |
| WO | WO-01/40291 A2 | 6/2001 |
| WO | WO-02/070007 A1 | 9/2002 |
| WO | WO-2004/000251 | 12/2003 |
| WO | WO-2004/002512 | 1/2004 |
| WO | WO-2004/098596 | 11/2004 |
| WO | WO-2005/080338 | 9/2005 |
| WO | WO-2006/059108 | 6/2006 |
| WO | WO-2006/075776 | 7/2006 |

OTHER PUBLICATIONS

Examination Report dated Jun. 18, 2020, received in related Australian Patent Application No. 2019203630 (5 pages).
Forsyth (1996) Thalidomide Responsive Chronic Pulmonary GVHD, Bone Marrow Transplant., 17:291-293.
Gerhardt, Susan G., et al. "Maintenance Azithromycin Therapy for Bronchiolitis Obliterans Syndrome: Results of a Pilot Study," Database Biosis [Online] Biosciences Information Service, Philadelphia PA, US; Database Accession No. PREV200300354152, Jul. 1, 2003 (2 pages).
Chung, K.F., "Cytokines as Targets in Chronic Obstructive Pulmonary Disease," Current Drug Targets, vol. 7, No. 6, Jun. 2006, pp. 675-681 (7 pages).
Park et al. (2004) Interleukin-1 Receptor Antagonist Attenuates Airway Hyperresponsiveness Following Exposure to Pzone, Am. J. Respir. Cell. Biol., 30:830-836.
Qin et al. (2000) In Vivo Evaluation of a Morpholino Antisense Oligomer Directed Against Tumor Necrosis Factor-alpha, Antisense & Nucleic Acid Drug Dev., 10:11-16.
Speich, Rudolf et al., "A Case Report of a Double-Blind, Randomized Trial of Inhaled Steroids in a Patient With Lung Transplant Bronchiolitis Obliterans," Database Biosis [Online] Biosciences Information Service, Database Accession No. PREV199799793547, Philadelphia, PA, US, 1997 (1 page).
Stenton et al. (2002) Inhibition of Allergic Inflammation in the Airways Using Aerosolized Antisense to Syk Kinase, J Immunol., 169:1028-1036.

(56) References Cited

OTHER PUBLICATIONS

Van Der Vaart et al. (2005) First Study of Infliximab Treatment in Patients With Chronic Obstructive Pulmonary Disease, Am. J. Respir. Grit. Care Med., 172:465-469.

Woo et al., (2005) VCAM-1 Upregulation via PKCdelta-p38 Kinase-Linked Cascade Mediates the TNF-alpha-induced Leukocyte Adhesion and Emigration in the Lung Airway Epithelium, Am J_ Physiol. Lung Cell Mol. Physiol., 288:L307-L310.

Trankle, C. R., et al., "IL-1 Blockade Reduces Inflammation in Pulmonary Arterial Hypertension and Right Ventricular Failure: A Single-Arm, Open-Label, Phase IB/II Pilot Study," American Journal of Respiratory and Crtiical Care Medicine, vol. 199, No. 3, pp. 381-384 (Feb. 1, 2019).

LOCALIZED THERAPY OF LOWER AIRWAYS INFLAMMATORY DISORDERS WITH PROINFLAMMATORY CYTOKINE INHIBITORS

CROSS REFERENCE TO RELATED APPLICATIONS

This application is a continuation of U.S. patent application Ser. No. 16/714,948, filed Dec. 16, 2019, which is a continuation of U.S. patent application Ser. No. 14/605,545, filed Jan. 26, 2015, patented on Feb. 4, 2020 as U.S. Pat. No. 10,550,389, which is a continuation of U.S. patent application Ser. No. 12/377,027, filed on Apr. 22, 2010, patented on Jan. 27, 2015 as U.S. Pat. No. 8,940,683, which is a National Stage Entry of International Patent Application No. PCT/US2007/017800, filed Aug. 10, 2007, which claims the benefit of U.S. Provisional Application No. 60/907,028, filed Mar. 16, 2007; U.S. Provisional Application No. 60/878,385, filed Jan. 4, 2007 and U.S. Provisional Application No. 60/836,760, filed Aug. 10, 2006, the contents of all of which are incorporated by reference.

FIELD OF THE INVENTION

The current invention relates to the use of proinflammatory cytokine inhibitors to treat inflammatory disorders of the lower airways.

BACKGROUND OF THE INVENTION

Chronic Obstructive Pulmonary Disease (COPD) is a major cause of morbidity and mortality worldwide. It is estimated that by 2020 COPD will be the third leading cause of mortality and fifth leading cause of morbidity (Malhotra et al. (2006) Expert. Opin. Emerg. Drugs 11(2):275-91). Overall health status and mortality are tightly associated with the severity of airflow obstruction. COPD is an inflammatory condition and neutrophil elastase has long been considered a significant mediator of the disease. Often, subjects are inadequately treated, resistant, or refractory to current therapies. COPD affects the peripheral airways and is associated with chronic irreversible obstruction of expiratory flow. This inflammatory disorder of the small airways includes chronic bronchitis (mucus hypersecretion with goblet cell and submucosal gland hyperplasia) and emphysema (destruction of airway parenchyma) associated with fibrosis and tissue damage.

Historically, treatments of COPD largely focused on addressing the symptoms of the condition especially exacerbations through acute antibiotic therapy, inhaled or oral corticosteroids, bronchodilators and more recently anti-cholinergics. While antibiotics are useful in treating the acute exacerbations of COPD, antibiotics alone do not eliminate the underlying often-chronic inflammation. Inhaled and oral corticosteroids have been used extensively to nonspecifically reduce the inflammatory conditions of the lower airways that play a critical role in COPD, but corticosteroids can cause serious side effects. These include thinning of membranes, bleeding, growth retardation in children, and osteoporosis; and when possible must be avoided or cautiously used with patients that have certain conditions, such as gastrointestinal ulcers, renal disease, hypertension, diabetes, osteoporosis, thyroid disorders, and intestinal disease. Nonetheless, steroids provide limited benefit in lower airways inflammatory disease associated with proinflammatory cytokines.

Cytokines are regulatory proteins produced in response to certain stimuli that act on receptors on the membrane of target cells. These regulatory proteins are generally described in references such as Cytokines, A. Mire-Sluis and R. Thorne, ed., Academic Press, New York, (1998). Recently, scientists have come to suspect that proinflammatory cytokines, in particular tumor necrosis factor alpha (TNF-alpha), may be the driving force behind numerous lower airways disorders. Increased levels of cytokines such as interleukin (IL)-6, IL-1beta, tumor necrosis factor-alpha (TNF-alpha) and IL-8 have been measured in sputum, with further increases occurring during exacerbations. Cytokines are also implicated involved in tissue remodeling. The cytokine profile seen in COPD is unique to these inflammatory disorders and differs from allergic disorders.

Numerous investigators have reported a potential role for nonallergic proinflammatory cytokines such as IL-8, IL-6, IL-1, and TNF in lower airways inflammatory disorders including COPD. IL-1 promotes inflammation by recruiting neutrophils to the lung. Inflammation persists with the release by neutrophils of additional IL-1 that upregulates the expression of other pro-inflammatory cytokines, chemokines, additional downstream inflammatory mediators such as e.g., neutrophil elastase (NE), mucous overproduction, tissue fibrosis, airways remodeling, and adhesion molecules including E-selectins and ICAM-1 that recruit additional neutrophils (Suzuki et al. (2002) Current Drug Targets—Inflammation & Allergy 1:117-26). Importantly, this IL-1b dependent "positive feedback" mechanism is thought to be critical in propagating the underlying inflammation in various pulmonary inflammatory disorders, likely including CF.

Another mechanism of IL-1b mediated inflammation is the promotion of reactive oxygen species via xanthine oxidase upregulation thought important in tissue fibrosis (Komaki (2005) Pulm. Pharmacol. Ther. 18(4):297-302). TGF-beta1 is believed to play an important role in the pathogenesis of a number of chronic inflammatory and immune lung diseases, including asthma, chronic obstructive pulmonary disease, and pulmonary fibrosis. IL-1beta-stimulated transcription of TGF-beta1 may play an important role in CF, other pulmonary inflammatory disorders, and sinusitis (Lee (2006) J. Immunol. 76(1):603-15).

Increases in IL-1b are closely associated with the severity of pulmonary disease (Chung (2006) Curr. Drug Targets. 7(6):675-81). IL-1b is produced by macrophages or epithelial cells upon exposures to stimuli like cigarette smoke or lipopolysaccharide from bacterial colonization in cystic fibrosis (CF). IL-1b also stimulates TNFalpha expression and many other downstream cytokines and chemokines and (de Boer (2005) DDT 10(2) 93-106) thus may regulate inflammatory pathways in the airways. Increased IL-1 is well documented in CF, smokers and in COPD patients at baseline and increases further with disease exacerbations (Chung (2005) Curr. Drug Targets Inflamm. Allergy 4(6): 619-25; Dal Negro et al. (2005) COPD 2(1):7-16; Tomaki et al. (2007) 20(5):596-605; Gessner et al. (2005) Respir. Med. 99(10):1229-40; Chung (2001), Eur. Respir. J. Suppl 34:50s-59s; Rusznak et al. (2000) Am. J. Respir. Cell Mol. Biol. 23:530-6). Pulmonary function tests (PFTs) are strongly associated with lung IL-1 lung levels (Ekberg-Jansson et al. (2001) Respir Med 95:363-73; Joos et al. (2001) Thorax 56:863-6). Recently, IL-1 and IL-1Ra haplotypes (genes) have been shown to differ in subjects with rapidly declining PFTs (Hegab et al. (2005) Biochem. Biophys. Res. Commun. 329 (4):1246-52).

In particular, lung NE may play a critical role downstream of IL-1. Overproduction of NE may promote inflammation and cause fibrosis in CF and other hereditary forms of COPD. Excess NE results in degradation of the lung epithelium with a resultant loss of pulmonary functions. NE also cleaves complement receptors hampering host defense mechanisms against further bacterial colonization in the lung (Tosi (1990) Clin. Invest. 86:300). The infection thereby becomes persistent, and the massive ongoing inflammation and excessive levels of NE destroy the airway epithelium, leading to the progressive loss of pulmonary function and death.

The inhibition of IL-1 in lung disease is expected to reduce lung neutrophil influx and decrease production and release of a myriad of pro-inflammatory molecules including NE. The normalization of inflammatory mediators including protease activity in the lung is likely to result in the preservation of elastin and alveolar architecture and improve or preserve lung functions.

In murine model systems, IL-1beta causes pulmonary inflammation, emphysema, and airway remodeling in the adult lung (Lappalainen et al. (2005) Am. J. Respir. Cell Mol. Biol. 32(4):311-8). Specifically, increased production of IL-1b in respiratory epithelial cells of adult mice causes increased neutrophils and lung inflammation, enlargement of distal airspaces, mucus metaplasia, and airway thickening and fibrosis in the adult mouse. IL-1Ra is the naturally occurring IL-1 inhibitor in lung, and decreases oxidative lung injury in rats (Leff et al. (1994) Am. J. Respir. Crit. Care Med. 150(1):109-12). IL-1Ra also protects in immune complex-induced lung injury (Shanley et al. (1996) J. Clin. Invest. 97: 963-70).

Systemic immunotherapy with proinflammatory cytokine inhibitors carries significant risks of immuno-suppression. Surprisingly, despite the extracellular actions of proinflammatory cytokines and their interactions with bronchial epithelial cells perpetuating the destructive inflammatory process, no one has described the advantages of localized delivery to the lung of proinflammatory cytokine inhibitors to treat inflammatory disorders of the lower airways including COPD. These advantages include, but are not limited to, better distribution of drug to affected airways, enhanced action given the localized production and action of these proinflammatory cytokines within the airways, and the avoidance of systemic side effects.

In COPD, the alveolar tissues and/or bronchiolar walls are progressively destroyed. This suggests cell death by necrosis and/or apoptosis. Based on a study concerning apoptosis-related factors in COPD patients, researchers have suggested that TNF-alpha, IL-6 and inflammation may be associated with progression of COPD (Yasuda (1998) Respir. Med. 92(8): 993-9). Additionally, IL-4 and TNF-alpha were found to be the only two cytokines present in the inflammatory infiltrate of patients with chronic bronchitis (Mueller et al. (1996) Respir. Med. 90(2):79-85), and it has been suggested that cytokine-bronchial epithelial cell interactions represent an important mechanism by which inflammatory events in the airway microenvironment can be regulated and represent potential targets for novel anti-inflammatory therapies in airway disorders (Levine (1995) Am. J. Respir. Cell Mol. Biol. 15(2):245-51).

Mucus overproduction and hypersecretion are characteristic of chronic bronchitis. Pathogenic factors associated with COPD, such as cigarette smoke, proinflammatory cytokines, and bacterial infections, can individually induce respiratory mucins in vitro and in vivo. Cigarette smoke has been suggested to have the potential to synergistically amplify induction of respiratory mucins by a proinflammatory stimuli relevant to COPD pathogenesis and contribute to mucin hyperproduction observed in patients with COPD. TNF-alpha has been implicated in acute smoke-induced inflammation and connective tissue breakdown, the precursor of emphysema (Churg et al. (2002) Am. J. Respir. Cell Mol. Biol. 27(3):368-74). TNF-alpha overexpression has also been found to have pleiotropic effects causing pathologic changes consistent with both emphysema and pulmonary fibrosis combined with a general lung inflammation (Lundblad et al. (2005) Am. J. Respir. Crit. Care Med. 171(2):1363-70).

It has been suggested that both TNF-alpha receptors contribute to the pathogenesis of COPD, but TNF-alpha receptor-2 is the most active receptor in the development of inflammation, emphysema, and systemic weight loss in this murine model of chronic obstructive pulmonary disease (D'hulst A I et al. (2006) Eur. Respir. J. 28(1):102-12).

Anticholinergic agents have recently been introduced as treatments for COPD. These agents provide symptomatic relief. Despite these benefits, anticholinergics do not treat the underlying inflammation in numerous disorders of the lower airways including COPD and associated problems including viscous secretions, and progressive lung destruction. Mucolytics, such as guaifenesin and N-acetyl cysteine, depolymerize mucin molecules, and are used to promote pulmonary drainage and are thought not to be detrimental. Like anticholinergics, mucolytics primarily provides symptomatic relief.

DNase has a number of known utilities and has been used for therapeutic purposes. Its principal therapeutic use has been to reduce the viscoelasticity of pulmonary secretions in such diseases as pneumonia and cystic fibrosis, thereby aiding in the clearing of the lower respiratory airways (Lourenco (1982) Arch. Intern. Med. 142(13):2299-308); Shak (1990) Proc. Natl. Acad. Sci. 87(23):9188-92); and Hubbard (1992) N. Engl. J. Med. 326(12):812-5). The utility of nucleases in COPD is limited however because these agents do not decrease inflammation nor do they treat the underlying etiologic agent.

More recently, lung reduction surgery has been used in COPD patients to improve the lung functions. While such surgery usually offers temporary relief of symptoms, it is typically not curative. Lung transplantation is also used in certain cases. Post-operative inflammation of the transplanted organs may be poorly controlled with broad acting immune modulators.

Nearly 65% of adults and 20% of children with CF have moderate to severe lung disease (CFF 2005). The CF lung is normal at birth but early in life, these subjects develop the onset of infection and inflammation. Defective Cl− re-absorption in the CF lung leads to desiccated airway secretions by drawing sodium (Na+) out of the airways, with water following. Abundant secretions interfere with mucociliary clearance by trapping bacteria in an environment that is well suited to colonization, with distinctive microbial pathogens (Reynolds 1976). The ensuing lung infection and inflammation recruits and activates neutrophils that ultimately release neutrophil elastase (NE) and other proteases. An excess of NE in the CF lung rapidly overwhelms normal levels of endogenous antiprotease. In addition, NE stimulates the production of pro-inflammatory mediators such as IL-1 that propagate inflammation.

Bronchiolitis obliterans syndrome (BOS) is another form of COPD and remains the leading cause of morbidity and mortality in the bone marrow and pulmonary transplant population. BOS is an inflammatory process of the airways identical with chronic allograft rejection and marked by progressive obstructive lung disease (Gerhardt et al. (2003)

Am. J. Respir. Crit. Care Med 68:121-5). BOS affects from 12 to 18% of lung transplant recipients at 1 year and up to 75% of individuals by 5 years (Kudoh et al. (1998) Am. J. Respir. Crit. Care Med. 157:1829-32; Culic et al. (2002) Eur. J. Pharmacol 450:277-89). Recent evidence suggests that the BAL neutrophilia is associated with BOS after lung transplant and the persistence of neutrophils in the airways predicts morbidity and mortality following lung transplant (Suzuki et al. (1999) Laryngoscope 109:407-10; Ianaro et al. (2000) J. Pharmacol. Exp. Ther. 292:156-63). Several studies have noted elevated levels of certain pro-inflammatory cytokines associated with bronchoalveolar lavage neutrophilia in BOS including IL-1b, TNF-a, and IL-8 (Ianaro et al. (2000) J. Pharmacol. Exp. Ther. 292:156-63; Scaglione et al. (1998) J. Antimicrob. Chemother 41(Suppl B):47-50; Suzuki et al. (1997) Laryngoscope 107:1661-66). Previous studies have also shown that anti-inflammatory macrolide antibiotics, such as erythromycin or azithromycin, may be efficacious in the treatment of bronchiolitis (Scaglione et al. (1998) J. Antimicrob. Chemother 41(Suppl B):47-50; Suzuki et al. (1997) Laryngoscope 107:1661-66). The suggested mechanism may include an indirect reduction in pro-inflammatory mediators in patients including interleukin (IL)-8, tumor necrosis factor-☐, and IL-1b (Verleden et al. (2006) Am. J. of Respir. Crit. Care Med. 174(5):566-70; Tsai et al. (2004) Am. J. Respir. Crit. Care Med. 170:1331-9; Yamada et al. (2000) Am. J. Rhinol. 4:143-8; Yates et al. (2005) Am. J. Respir. Crit. Care Med. 172:772-5; Estenne et al. (2002) J. Heart Lung Transplant 21:297-310; Shitrit et al. (2005) J. Heart Lung Transplant 24:1440-3; Verleden et al. (2004) Transplantation 77:1465-7). While macrolide antibiotics may be useful in BOS because of their nonspecific anti-inflammatory activities, low-dose maintenance therapy with these agents may lead to broad antibiotic resistance, crippling our healthcare system.

New targeted anti-inflammatory therapies are needed to improve long-term patient outcomes after transplantation because BOS treatment options are lacking. Disrupting the positive feedback loop of neutrophil driven lung destruction represents a potentially transformational therapeutic approach to BOS whereby functional and anatomical organ preservation may be improved with the use of inhaled proinflammatory cytokine inhibitors.

Importantly, the results from clinical trials of macrolides in BOS as indirect inhibitors of pro-inflammatory cytokines can be helpful in estimating the anticipated treatment effect, treatment duration, and sample size required for trials with inhaled proinflammatory cytokine inhibitors in this disorder. Macrolides are reported to decrease cytokine production, reduce neutrophils recruitment, and improve FEV1 (Verleden et al. (2006) Am. J. of Respir. Crit. Care Med. 174(5):566-70). For example, an open-label pilot trial showed 5 of 6 patients (83%) demonstrated significant improvement in FEV1 (mean improvement of 0.50 L (range 0.18 to 1.36 L) or 17%; P<0.05), as compared with their baseline values at the start of azithromycin therapy over a mean of 13.7 weeks (Verleden et al. (2006) Am. J. of Respir. Crit. Care Med. 174(5):566-70). The study by Verleden et al., in 14 BOS patients showed significantly decrease neutrophilia 30% (P=0.002); and BAL IL-8 levels (P=0.04); and FEV1 increased greater than 13% (P=0.007) in six responders of 14 (43%), after 3 months of macrolide treatment. Yates et al. (2005) Am. J. Respir. Crit. Care Med. 172:772-5, were able to show a significant but variable improvement in the FEV1 of mean 110 ml (range, −70 to 730 ml) between baseline and after 3 months of azithromycin therapy P<0.002). This improvement was sustained beyond 3 months in 12 of 17 (71%) patients (up to 11 months follow-up). Khalid et al. (2005) Eur. Respir. J. 25(3):490-3, in another series of 8 patients showed clinically significant improvements (greater than 10% improvement) in 87% (7 of 8 subjects) in both forced vital capacity (FVC), where the mean (95% confidence interval) increase reported was 410 mL (0.16-0.65), which was an average improvement of 21.57%, and in the forced expiratory volume in one second (FEV1), where the mean increase noticed was 280 mL (0.10-0.44), which was an average improvement of 20.58%. Similar past studies show a mean FEV1 increase at around three months of 18% in 8 subjects; a mean increase of 14% in 20 subjects (18); and no improvement in FEV1 in 11 subjects.

Recently, a dramatic response to a pro-inflammatory cytokine inhibitor was published in a case study (Fullmer et al. (2005) Pediatrics 116:767-70). These one-off data further support the use of this class of agent in BOS, however, they do not overcome the limitations of systemic administration.

Very recently, van der Vaart et al. (2005) Am. J. Respir. Crit. Care Med. 172(4): 465-9, ran the first clinical trial of a proinflammatory cytokine inhibitor, infliximab (a monoclonal anti-TNF-alpha antibody with demonstrated efficacy in other autoimmune diseases, such as Crohn's disease and rheumatoid arthritis). Based on the lack of benefit of the systemic administration of this proinflammatory cytokine inhibitor in the diseased patients, it is expected that the local administration of infliximab and other proinflammatory cytokine inhibitors will provide better clinical benefits with minimal side effects. The localized nature of the COPD disorder and the need for localized therapy was further underscored by Schmidt-Ioanas et al. (2006) Respir. Med. 100(4):639-47. The local production and extracellular actions in the airways of proinflammatory cytokines provides a unique opportunity for localized therapy representing a novel and significant improvement over systemic proinflammatory cytokine inhibitor therapies for lower airways inflammatory disorders.

The lack of clinical benefit in the first trial of a systemic proinflammatory cytokine inhibitor is consistent with well-recognized limitations of systemic dosing to attain desirable levels of drug in the lung parenchyma and airways, where the local actions of proinflammatory cytokines such as IL-1 b and TNF-alpha are critical in inflammatory disorders. Moreover, immunosuppression due to the systemic administration of proinflammatory cytokine inhibitors, for example TNF-alpha inhibitors, is well described to predispose patients to serious complications including death. This is especially important in already compromised patients including those commonly suffering with inflammatory disorders of the lower airways including COPD.

Given the unmet need and the huge impact on public health resources, better treatments are needed to prevent or speed the recovery of individuals suffering with COPD. Indeed, better treatments are needed to control inflammation that causes lung destruction and to facilitate the clearance of viscous secretions whereby individuals at risk or affected with inflammatory conditions of the lower airways including COPD, suffer less. What is needed are new therapies that incorporate a composition including, but not limited to, a proinflammatory cytokine inhibitor and when appropriate, one or more additional therapeutically effective compounds capable of treating COPD locally; and a delivery device to expressly distribute the composition to the lower airways.

Furthermore, no article of manufacture and method for delivery expressly to the lower airways has been described including a composition that contains a proinflammatory cytokine inhibitor, and when appropriate for the subject other pharmacologically active agents that have the desirable actions described herein. The current invention answers this important unmet need whereby it incorporates a composition including but not limited to a proinflammatory cytokine inhibitor, and when appropriate, one or more additional therapeutically effective compounds capable of treating COPD; a delivery device for expressly distributing said composition to the lower airways to control inflammation, lung destruction and when appropriate treat other problems associated with "COPD" including inflammation, infection, and viscous secretions.

SUMMARY OF THE INVENTION

The present invention is drawn to methods and compositions for treating inflammatory disorders of the lower airways, comprising administering an effective amount of an agent which modulates the expression and/or activity of a proinflammatory cytokine or fragment thereof, preferably in a human. In a preferred embodiment, the inflammatory disorder of the lower airways is chronic obstructive pulmonary disease (COPD).

The agent may be administered via inhalation. In a preferred embodiment thereof, inhalation is carried out with a nebulizer, an inhaler, a sprayer, a powder dispenser or a dry powder generator. In another preferred embodiment, the agent is administered via direct instillation into the lower airways and in a specific embodiment thereof, direct instillation is carried out by intratracheal or mucosal administration. In a further embodiment, the direct instillation is carried out with an intrapulmonary aerosolizer or a sub-miniature aerosolizer.

Preferably, the expression of the proinflammatory cytokine is decreased. In another embodiment, the activity of the proinflammatory cytokine is decreased. In a further preferred embodiment, the agent is a proinflammatory cytokine inhibitor. In a particular embodiment, the effective amount comprises 0.1 mg to 100 mg of the proinflammatory cytokine inhibitor. The proinflammatory cytokine inhibitor may be siRNA or antisense nucleic acid; for example, the antisense nucleic acid is antisense to IL-1, IL-6, IL-8, TNF or TNF-alpha.

In some embodiments of the present invention, the agent is an antibody. In a preferred embodiment, the antibody is selected from a group consisting of a humanized antibody, a chimeric antibody, a monoclonal antibody, a polyclonal antibody and an antibody fragment. In a specific embodiment thereof, the antibody binds IL-1, IL-6, IL-8 or TNF-alpha. In another embodiment, the proinflammatory cytokine inhibitor is an IL-1 receptor antagonist-like molecule selected from a group of consisting of IL-Hy1, IL-1Hy2 or IL-1 TRAP. In still another embodiment, the proinflammatory cytokine inhibitor is a soluble cytokine receptor protein and in a particular embodiment, the soluble cytokine receptor protein may be a soluble TNF receptor protein. In a further embodiment, the soluble cytokine receptor protein is a soluble TNF-alpha receptor protein. In a preferred embodiment, the proinflammatory cytokine inhibitor may be a soluble IL-1 receptor protein and in a specific embodiment thereof, the IL-1 receptor antagonist is anakinra.

The present invention also contemplates that the proinflammatory cytokine is IL-1.

In another embodiment of the present invention, the proinflammatory cytokine is TNF and in a particular embodiment thereof, the proinflammatory cytokine is TNF-alpha.

Another aspect of the present invention is a kit comprising a delivery device suitable for direct administration of a pharmaceutical composition to the lower airways and a pharmaceutical composition comprising a therapeutically effective amount of at least one proinflammatory cytokine inhibitor and at least one pharmaceutically acceptable carrier. In a preferred embodiment, the delivery device is selected from group consisting of a nebulizer, an inhaler, a sprayer, or a powder dispenser. In another preferred embodiment, the delivery device is an intrapulmonary aerosolizer or sub-miniature aerosolizer. In some embodiments, the therapeutically effective amount comprises 0.1 mg to 100 mg of the proinflammatory cytokine inhibitor. The proinflammatory cytokine inhibitor contemplated by the inventions is an antisense nucleic acid, which is antisense to IL-1, IL-6, IL-8 or TNF-alpha. The proinflammatory cytokine inhibitor may be an antibody such as e.g., a humanized antibody, a chimeric antibody, a monoclonal antibody, a polyclonal antibody and an antibody fragment. In an embodiment, the antibody binds IL-1, IL-6, IL-8 or TNF-alpha. The proinflammatory cytokine inhibitor may be an IL-1 receptor antagonist-like molecule such as e.g., IL-Hy1, IL-Hy2 or IL-1 TRAP. In still another embodiment, the proinflammatory cytokine inhibitor is a soluble cytokine receptor protein that may be a soluble TNF receptor protein. Specifically, the soluble cytokine receptor protein may be a soluble TNF-alpha receptor protein or a soluble IL-1 receptor protein, particularly the soluble IL-1 receptor antagonist may be anakinra.

The present invention is also drawn to a pharmaceutical composition suitable for direct administration to the lower airways, comprising a therapeutically effective amount of at least one proinflammatory cytokine inhibitor, at least one-second active ingredient, and at least one pharmaceutically acceptable carrier. In a preferred embodiment, the therapeutically effective amount comprises from about 0.1 mg to about 100 mg of the proinflammatory cytokine inhibitor. In another embodiment, the proinflammatory cytokine inhibitor may be an antisense nucleic acid or siRNA. In a particular embodiment, the antisense nucleic acid is antisense to IL-1, IL-6, IL-8, TNF or TNF-alpha.

In some embodiments, the proinflammatory cytokine inhibitor is an antibody and in a specific embodiment, the antibody is selected from a group consisting of a humanized antibody, a chimeric antibody, a monoclonal antibody, a polyclonal antibody and an antibody fragment including single chain antibodies. In a further embodiment thereof, the antibody binds IL-1, IL-6, IL-8, TNF or TNF-alpha. In another preferred embodiment, the proinflammatory cytokine inhibitor is an IL-1 receptor antagonist-like molecule such as e.g., IL-Hy1, IL-Hy2 or IL-1 TRAP. In still another preferred embodiment, the proinflammatory cytokine inhibitor is a soluble cytokine receptor protein. In a particular embodiment, the soluble cytokine receptor protein is a soluble TNF receptor protein. In a preferred embodiment, the soluble cytokine receptor protein is a soluble TNF-alpha receptor protein. In a further preferred embodiment, the soluble cytokine receptor protein may be a soluble IL-1 receptor protein and in a specific embodiment thereof, the soluble IL-1 receptor antagonist is anakinra. In some embodiments, the second active ingredient is selected from a group consisting of an amiloride, an antibiotic, an antihistamine, an anticholinergic, an anti-inflammatory agent, a mucolytic, and a steroid.

DETAILED DESCRIPTION

The invention provides an article of manufacture and methods for formulating and treating lower airways disorders comprising administering to a mammal diagnosed as having COPD and in need of treatment an effective amount of a composition comprising: at least one proinflammatory cytokine inhibitor, pharmaceutically acceptable carrier, and a delivery device capable of expressly delivering said compositions to the lower airways avoiding the complications of systemic delivery. The compositions may contain a one or more active ingredient such as a proinflammatory cytokine inhibitor that may be administered to the mammal in need of treatment, or alternatively, may contain one or more additional pharmacologic agents capable of reducing inflammation, secretions, infection, obstruction, or hydrating secretions. The invention also provides methods for formulating a composition containing a proinflammatory cytokine inhibitor with an effective amount of one or more pharmacologic agents including non-limiting examples of an anti-inflammatory, antibiotics, steroids, surfactants, hydrating agents, and other pharmacologically active and inactive compounds.

Although not being bound by any particular theory, it is presently believed the said invention can be used to reduce substantially the inflammatory process underlying the progressive loss of lung functions and exercise capacity, and other associated symptoms, thereby treating the pathologic conditions associated with COPD.

The present invention also relates generally to methods of preparation of liquid solutions of proinflammatory cytokine inhibitors that are protected from thermally induced aggregation of the cytokine inhibitor component. The present invention relates additionally to the general preparation of liquid solutions of proinflammatory cytokine inhibitor(s) that are maintained stable at neutral pH or less than neutral pH, and most preferred at room temperature or controlled room temperature.

The invention further provides articles of manufacture and kits that include a container, a delivery device; a label on said container and/or a device capable of delivering said composition to the lower airways contained within said container or delivery device that includes one or more active ingredients as described herein, a pharmaceutically-acceptable carrier; and instructions for using said composition for expressly treating lower airways inflammatory disorders or pathologic conditions of the lower airways by avoiding systemic delivery and the complications of systemic immunotherapy.

The current invention circumvents the limitations of systemic administration of proinflammatory cytokine inhibitors providing higher levels of drug locally where the extracellular proinflammatory cytokines act, avoiding the systemic exposures and potential complications of these powerful immunotherapies. The current invention teaches the addition of a proinflammatory cytokine inhibitor, to the pre- intra- and post-operative care of subjects with lower airways inflammatory disorders including COPD. One aspect of the current invention is a device for local delivery expressly to the lower airways of a composition including at least a proinflammatory cytokine inhibitor with the potential co-administration of other active compounds to treat lower airways inflammatory disorders including COPD peri-operarively, or chronically as a part of their therapy.

Definitions

The term "proinflammatory cytokine" refers to cytokines that generally promote inflammatory processes including but not limited to IL-6, IL-8, TNF and IL-1 that differ from allergic cytokines in their structure and functions. These proinflammatory cytokines are further described as TNF-Homo Tumor necrosis factor; Tumor necrosis GenBank, P01375 alpha sapiens factor ligand superfamily member 2; SWISSPROT TNF-a; Cachectin TNF-Mus Tumor necrosis factor; Tumor necrosis GenBank, P06804 alpha factor ligand superfamily member 2; SWISSPROT TNF-a; Cachectin TNF-RI Homo Tumor necrosis factor receptor GenBank, P19438 sapiens superfamily member 1A; p60; TNF-R1; SWISSPROT p55; CD120a (contains: Tumor necrosis factor binding protein 1 (TBPI)), TNF-RI Mus Tumor necrosis factor receptor GenBank, P25118 superfamily member 1A; p60; TNF-R1; SWISSPROT p55 TNF-RII Homo Tumor necrosis factor receptor superfamily GenBank, P20333 sapiens member 1B; Tumor necrosis factor receptor SWISSPROT 2; p80; TNF-R2; p75; CD120b; Etanercept (contains: Tumor necrosis factor binding protein 2 (TBPII)), TNF-RII Mus Tumor necrosis factor receptor GenBank, P25119 superfamily member 1B; Tumor necrosis SWISSPROT factor receptor 2; TNF-R2; p75 IL-1 alpha Homo Interleukin-1 alpha; Hematopoietin-1 GenBank, P01583 sapiens SWISSPROT IL-1 alpha Mus Interleukin-1 alpha GenBank, P01582 SWISSPROT IL-1 R-1 Homo Interleukin-1 receptor, type I; IL-1R-GenBank, P14778 sapiens alpha; P80; Antigen CD121a SWISSPROT IL-1 R-1 Mus Interleukin-1 receptor, type I; P80 GenBank, P13504 SWISSPROT IL-1 R-2 Homo Interleukin-1 receptor, type II; IL-1R-GenBank, P27930 sapiens beta; Antigen CDw121b SWISSPROT IL-1 R-2 Mus Interleukin-1 receptor, type II GenBank, P27931 SWISSPROT.

As defined herein, the term "proinflammatory cytokine inhibitor(s)" or "proinflammatory cytokine antagonist" includes a "tumor necrosis factor neutralizing antibody", "TNF antagonist", "TNF antibody", "TNF-alpha antibody", "TNF-beta antibody", "TNF inhibiting antibody", "TNF inhibitor", "IL-6 inhibitor", "IL-6 antibody", "IL-6 antagonist", "IL-8 inhibitor", "IL-8 antibody", "IL-8 antagonist", "IL-1 inhibitor", "IL-1 antibody", "IL-1 antagonist", "IL-1 receptor antagonist", "anti-IL-1 receptor antibody", "TNF-alpha receptor antagonist", "anti-TNF-alpha receptor antibody," "soluble IL-1 receptor," "soluble TNF-alpha receptor," "IL-1 mutein," "TNF alpha mutein," "IL-1RNAi, "TNF-alpha RNAi" or fragment of any of the foregoing is a compound that can decrease, inhibit, block, abrogate, interfere, prevent a proinflammatory cytokine production and/or synthesis, membrane cleavage, release, receptor signaling, or in general inhibit the activity, including one or more forms of the proinflammatory cytokine.

These terms as used herein incorporate "mature", "pre", "pre-pro", "pro", "fragments" and "variant" forms of a protein, purified from a natural source, chemically synthesized or recombinantly produced.

Multiple human proinflammatory cytokine variants have been described and in certain instances, proinflammatory cytokine inhibitors that recognize these variants. It will be understood that natural allelic variations exist and can occur among individuals, as demonstrated by one or more amino acid differences in the amino acid sequence of each individual. Allelic variations are specifically encompassed herein. Moreover, fragments either naturally occurring or engineered with all, substantially all, or a significant portion of proinflammatory cytokine inhibitor activity where the proinflammatory cytokine inhibitor may be helpful as a treatment of lower airways disease, are also encompassed herein.

The term "upper airways" or the "upper respiratory tract" when used herein refers to or describes the anatomic regions including the passageways from nares or nostrils to the soft palate and includes the sinuses.

The term "lower airways" or lower respiratory tract" when used herein refers to or describes the anatomic regions below the larynx including the trachea and lungs.

The term "pharynx" or "posterior pharynx" when used herein refers to or describes the anatomic regions above the trachea and up to the soft palate, but excludes the upper airways.

The term "cystic fibrosis" or "CF" when used herein refers to or describes the physiological and pathologic condition in mammals typically characterized by viscous mucus secretions that tend to obstruct or occlude various internal passageways in a mammal, including but not limited to, the sinuses, lower airways, pancreatic ducts, bile ducts, and intestinal tract. This condition is typically associated with a genetic variant of the cystic fibrosis transmembrane receptor gene and protein.

The terms "treating", "treatment," and "therapy" as used herein refer to curative therapy, prophylactic therapy, and preventative therapy.

The term "mammal" as used herein refers to any animal classified as a mammal, including humans, cows, horses, dogs and cats. In a preferred embodiment of the invention, the mammal is a human.

As used herein, "a" or "an" means at least one, unless clearly indicated otherwise. The term "about," unless otherwise indicated, refers to a value that is no more than 10% above or below the value being modified by the term. For example, the term "about 5% (w/w)" means a range of from 4.5% (w/w) to 5.5% (w/w).

As used herein, unless indicated otherwise, the terms "compound" and "compound of the invention" refers to a substance within the composition of the invention including proteins and small molecules.

As used herein, unless indicated otherwise, the term "COPD" and lower airways "inflammatory disorder(s)" refers to any nonallergic (IgE mediated) inflammatory condition of the lower airways that include but are not limited to acute and chronic bronchitis, bronchiolitis, emphysema, Still's disease, Wegener's disease, Behcet's disease, keratoscleritis, lymphomatous tracheo-bronchitis, and Cogan's syndrome and the like.

As used herein the terms "proinflammatory cytokine inhibitor(s)", "TNF antagonist(s)", "TNF inhibitor(s)", "cytokine inhibitor(s)" or "cytokine antagonist(s)", or "inhibitor(s)" according to the present invention refers to one or more agents (i.e., molecules or compounds) that inhibit or block the activity of TNF, IL-1, IL-6 or IL-8. The term "antagonist" is used synonymously with the term "inhibitor." The antagonists of the present invention act by blocking or reducing cytokine signal transduction, or by reducing or preventing expression of the cytokine or its receptor. Antagonists include agents that bind to the cytokine itself, and compounds that bind one or more subunits of the cytokine receptor. For example, inhibitors include antagonistic antibodies or antibody fragments including single chain antibodies that bind the cytokine itself, antagonistic antibodies or antibody fragments that bind one or more subunits of the cytokine receptor, soluble ligands that bind to the receptor, soluble receptors that bind to the cytokine, as well as aptamers, small molecules, peptidomimetics, and other inhibitory agents capable of binding the cytokine or its receptor. Antagonists also include molecules that reduce or prevent expression of the cytokine, its receptor, or a receptor subunit. These antagonists include antisense oligonucleotides that target mRNA, and interfering messenger RNA. Additional antagonists include compounds that prevent and/or inhibit proinflammatory cytokine synthesis, their release or their actions on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit proinflammatory cytokine receptor signaling, such as mitogen activated protein (MAP) kinase inhibitors; compounds which block and/or inhibit membrane proinflammatory cytokine cleavage, such as various metalloproteinase inhibitors; compounds which block and/or inhibit proinflammatory cytokine activity, such as angiotensin converting enzyme (ACE) inhibitors (e.g., captopril); and compounds which block and/or inhibit certain proinflammatory cytokines production and/or synthesis, such as ERK or MAP kinase inhibitors. The term "proinflammatory cytokine inhibitor" also encompasses agents, which modulate the expression and/or activity of a proinflammatory cytokine.

Additional non-limiting examples of suitable specific proinflammatory cytokine antagonists are known and are incorporated in their entirety herein. These include but are not limited to entanercept (ENBREL), sTNF-RI, onercept, D2E7, and REMICADE, and antibodies specifically reactive with TNF-alpha and TNF-alpha receptor. Antagonists include IL-1 antagonists including IL-1ra molecules such as e.g., anakinra, KINERET, and IL-1ra-like molecules such as IL-1Hy1 and IL-1Hy2; IL-1 "trap" molecules (as described in U.S. Pat. No. 5,844,099); IL-1 antibodies; CDP 484, ACZ885 (anti-interleukin-1beta monoclonal antibody), Hu007 (IL-1b Ab)—Phase II Rheumatoid Arthritis (Lilly), AMG-108 (IL-1R Ab), solubilized IL-1 receptor, polypeptide inhibitors to IL-1 alpha and IL-1 alpha receptor; and anti-IL-8 antibodies (e.g., ABX-IL-8 (Abgenix)).

As used herein, unless indicated otherwise, the term "drug substance" refers to one or more "active ingredients" or "compounds including biologics" that are intended to furnish pharmacological activity or other direct effect in the diagnosis, cure, mitigation, treatment, or prevention of disease or to affect the structure or any function of the human body.

As used herein, unless indicated otherwise, the terms "composition" and "composition of the invention", are used interchangeably. Unless stated otherwise, the terms are meant to encompass, and are not limited to, pharmaceutical compositions and nutraceutical compositions containing drug substance. The composition may also contain one or more "excipients" that are "inactive ingredients" or "compounds" devoid of pharmacological activity or other direct effect in the diagnosis, cure, mitigation, treatment, or prevention of disease or to affect the structure or any function of the human body.

As used herein, the term "natural source" refers to a material that occurs in the natural environment, or biologic manufactured substances in a host organism and may comprise one or more biological entities. For example, a natural source can be a plant, an animal, an anatomical part of a plant or animal, a microorganism, a mixture of different plants, animals, and/or microorganisms, or an environmental sample. It is not necessary that the biological entities present in a natural source be classified or characterized. The term also refers to compositions that have been prepared directly from that which occurs in the natural environment by a process that does not selectively remove or retain one or more specific compounds relative to the other different compounds.

It is contemplated that, where the compound(s) of the invention occur in a natural source, the terms "composition" and "composition of the invention" may encompass a physically and/or chemically modified form of the natural source or host organism. For example, if the compound(s) can be obtained from an organism, the terms are not intended to encompass the organism or an anatomical part of the organism, however, a powder or a solvent extract of the organism or organism part(s) can be a compound of the invention or compound of the composition of the invention herein.

As used herein, a "functional equivalent", "derivative", "fragment" or "region" of a proinflammatory cytokine or its receptor, including the cytokine receptor molecules, refers to the portion of the cytokine receptor molecule, or the portion of the cytokine receptor molecule sequences that encodes the cytokine receptor molecule, that is of sufficient size and sequences to functionally resemble the cytokine receptor molecules that can be used in the present invention as noted herein.

As used herein, the term "vehicle" refers to a diluent, adjuvant, excipient, carrier, or filler with which the compound or composition of the invention is stored, transported, and/or administered.

As used herein, the phrase "pharmaceutically acceptable salt" refers to pharmaceutically acceptable organic or inorganic salts of a compound of the invention.

As used herein, the term "pharmaceutically acceptable solvate" refers to an association of one or more solvent molecules and a compound of the invention. Examples of solvents that form pharmaceutically acceptable solvates include, but are not limited to water, saline, water-salt mixtures, isopropanol, ethanol, methanol, DMSO, ethyl acetate, acetic acid, polyethelene glycol and ethanolamine.

As used herein, the term "pharmaceutically acceptable" means approved by a regulatory agency of the Federal or a state government or listed in the U.S. Pharmacopeia or other generally recognized pharmacopeia for use in animals, and more particularly in humans.

The term "hydrating agent" or "hydrating substance" as used herein includes but is not limited to saline, hypertonic saline, polyethylene glycol or glycerol.

Pharmaceutical Compositions of the Invention

The present invention provides for the treatment of lower airways disorders including COPD with compositions comprising an agent, which modulates the expression and/or activity of a proinflammatory cytokine (such as e.g., a proinflammatory cytokine inhibitor and/or antagonist), and methods of using the compositions. The composition may further comprise of a pharmaceutically acceptable carrier, and delivery device referred to hereinafter as the "composition." The composition will be particularly useful for the treatment of mammals having a pathological pulmonary condition that is accompanied by abnormal pulmonary functions, inflammation, viscous, or inspissated mucus secretions or fluid absorption by lower airway cells. Examples of such conditions include but are not limited to forms of COPD including emphysema, acute, subacute or chronic bronchitis, bronchiolitis, Still's disease, Wegener's disease, Behcet's disease, keratoscleritis, lymphomatous tracheobronchitis, and Cogan's syndrome, and cystic fibrosis.

The composition useful in the practice of the present invention can be prepared in a number of ways. For instance, the composition can be prepared using an isolated or purified form of proinflammatory cytokine inhibitor. Methods of isolating and purifying proinflammatory cytokine inhibitor from natural sources are known in the art. Alternatively, a proinflammatory cytokine inhibitor can be chemically or biologically synthesized and prepared using recombinant DNA techniques that are well known in the art. These isolation and purification methods can be employed for obtaining proinflammatory cytokine inhibitor from various tissues, recombinant manufacturing processes, and transgenic animals.

In one embodiment, the pharmaceutical composition comprises at least one proinflammatory cytokine inhibitor, as well as optionally, at least one second active ingredient, and at least one pharmaceutically acceptable carrier. In a preferred embodiment, the proinflammatory cytokine inhibitor is an antisense nucleic acid.

The proinflammatory cytokine inhibitor may be from human or any non-human species. For instance, a mammal may have administered proinflammatory cytokine inhibitor from a different mammalian species (e.g., rats can be treated with human proinflammatory cytokine inhibitor). Preferably, however, the mammal is treated with homologous proinflammatory cytokine inhibitor (e.g., humans are treated with human proinflammatory cytokine inhibitor) to avoid potential immune reactions to the proinflammatory cytokine inhibitor. More preferred is when the mammal is treated with a proinflammatory cytokine inhibitor with at least 80% homology to the native proinflammatory cytokine inhibitor or fragment. Still more preferred is when the mammal is treated with a proinflammatory cytokine inhibitor with at least 90% homology to the native proinflammatory cytokine inhibitor or fragment. Still more preferred is when the mammal is treated with a proinflammatory cytokine inhibitor or fragment with at least 95% homology to the native proinflammatory cytokine inhibitor. Most preferred is when the mammal is treated with a proinflammatory cytokine inhibitor or fragment with 99% or greater homology to the native source of protein.

Exemplary proinflammatory cytokine inhibitors include proteins, polypeptides, peptides, fusion proteins, antibodies (e.g., human, humanized, chimeric, monoclonal, polyclonal, Fvs, ScFvs, Fab fragments, F(ab)sub2 fragments, and antigen-binding fragments thereof) such as antibodies that immunospecifically bind to TNF, TNF-alpha, IL-6, IL-8 or IL-1, cyclosporin, macolides, ketolides, tacrolimus (Rapamune), nucleic acid molecules (e.g., antisense molecules or triple helices), organic molecules, inorganic molecules, and small molecules that block, reduce, inhibit or neutralize a function, an activity and/or the expression of TNF, TNF-alpha, IL-6, IL-8 or IL-1. The proinflammatory cytokine inhibitor may be an antibody, protein, or small molecule. In a preferred embodiment, the antibody is a humanized antibody, a chimeric antibody, a monoclonal antibody, a polyclonal antibody or an antibody fragment.

The present invention also contemplates the use of TNF human antibody. A non-limiting example of a suitable TNF human antibody of the present invention can bind TNF-alpha and includes anti-TNF antibodies, antigen-binding fragments thereof, and specified variants or fragments thereof that bind specifically to TNF.

Additional TNF antagonists suitable for compositions, combination therapy, co-administration, devices and/or methods of the present invention, include, but are not limited to receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as various metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as ERK or MAP kinase inhibitors.

The present invention also contemplates includes the use of IL-1 and IL-1R human antibody. A non-limiting example of a suitable IL-1 human antibody of the present invention can bind IL-1 and includes anti-IL-1 and IL-1R antibodies, antigen-binding fragments thereof, and specified variants or fragments thereof that bind specifically to IL-1 or its receptors. Additional IL-1 antagonists suitable for compositions, combination therapy, co-administration, devices and/or methods of the present invention, include, but are not limited to receptor molecules which bind specifically to IL-1; compounds which prevent and/or inhibit IL-1 or IL-1R synthesis, IL-1 or IL-1R release or its pleiotropic actions on target cells.

In another embodiment, the pharmaceutical composition of this invention comprises a proinflammatory cytokine inhibitor, which may be a soluble cytokine receptor protein. The soluble cytokine receptor protein may be a soluble TNF-alpha receptor protein or a soluble IL-1 receptor protein. The soluble IL-1 receptor protein may be anakinra.

One, or multiple proinflammatory cytokine antagonists can be used in the compositions and methods of this invention. In various embodiments, a cytokine antagonist reduces the function, activity and/or expression of a proinflammatory cytokine by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

Examples of antibodies that immunospecifically bind to TNF-alpha include, but are not limited to, D2E7 (Abbott Laboratories/Knoll Pharmaceuticals Co., Mt. Olive, N.J.); CDP571 which is also known as HUMICADE and CDP-870 (both of Celltech/Pharmacia, Slough, U.K.); infliximab, and TN3-19.12 (Thorbecke et al. (1992) Proc. Natl. Acad. Sci. 89(16):7375-9; Williams et al. (1994) Proc. Natl. Acad. Sci. 91(7):2762-6). The present invention also encompasses the use of the antibodies that immunospecifically bind to TNF-alpha disclosed in the following U.S. patents in the compositions and methods of the invention: U.S. Pat. Nos. 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787; each of which are herein incorporated by reference in their entirety. Examples of soluble TNF-alpha receptors include, but are not limited to, sTNF-R1, etanercept and its rat homolog, soluble inhibitors of TNF-alpha derived from TNFrI, TNFrII (Kohno et al. (1990) Proc. Natl Acad. Sci. 87(21):8331-5)), and TNF-alpha Inh (Seckinger et al. (1990) Proc. Natl. Acad. Sci. 87(13):5188-92); Kohno et al. (1990) Proc. Natl. Acad. Sci. 87(21) 8331-5).

In another embodiment, a soluble proinflammatory cytokine receptor is used in the compositions and methods of the invention. In a specific embodiment, a TNF-alpha inhibitor used in the compositions and methods of the invention is etanercept or a fragment, derivative or analog thereof. In another embodiment, an antibody that immunospecifically binds to TNF-alpha that is a TNF-alpha inhibitor is used in the compositions and methods of the invention. In a specific embodiment, a TNF-alpha antagonist used in the compositions and methods of the invention is infliximab a derivative, analog or antigen-binding fragment thereof.

Other TNF-alpha and IL-1 antagonists encompassed by the invention include, but are not limited to, thalidomide, macrolides and ketolides such as e.g., tacroliums (Rapamune), antisense molecule 104838 (ISIS), IL-10 (Oswald et al. (1992) Proc. Natl. Acad. Sci. 89(18): 8676-80), quinacrine (mepacrine dichlorohydrate), the murine product TBP-1 (Serono[Yeda]), the vaccine CytoTAb, the peptide RDP-58, CDC-801, DPC-333, VX-745, AGIX-4207, ITF-2357, NPI-13021-31, SC10-469, TACE targeter, CLX-120500, Thiazolopyrim, auranofin, TNFR-IgG (Ashkenazi et al. (1991) Proc. Natl. Acad. Sci. 88(23):10535-9), tenidap, and anti-p38 MAPK agents.

Suitable proinflammatory cytokine inhibitors include e.g., entanercept (ENBREL), sTNF-RI, onercept, D2E7, and REMICADE, antibodies specifically reactive with TNF-alpha and TNF-alpha receptor, IL-1 antagonists including IL-1ra molecules such as e.g., anakinra, KINERET, and IL-1ra-like molecules such as IL-1Hy1 and IL-1Hy2; IL-1 "trap" molecules (as described in U.S. Pat. No. 5,844,099); IL-1 antibodies; CDP 484, ACZ885 (anti-interleukin-1beta monoclonal antibody), Hu007 (IL-1b Ab)—Phase II Rheumatoid Arthritis (Lilly), AMG-108 (IL-1R Ab), solubilized IL-1 receptor, polypeptide inhibitors to IL-1 alpha and IL-1 alpha receptor; and anti-IL-8 antibodies (e.g., ABX-IL-8 (Abgenix)).

Additional suitable proinflammatory cytokine antagonists include macrolides, such as e.g., erythromycin azithromycin (Zithromax, Zitromax), clarithromycin (Biaxin), dirithromycin (Dynabac), roxithromycin (Rulid, Surlid), developmental macrolides, such as e.g., carbomycin A, josamycin, kitasamycin, oleandomycin, spiramycin, troleandomycin, tylosin/tylocine (Tylan), midecamicine/midecamicine acetate, ketolides, such as e.g., telithromycin (Ketek), cethromycin, spiramycin, ansamycin, oleandomycin, carbomycin and tylocine, and non-antibiotic macrolides, such as e.g., tacrolimus (Rapamune).

In accordance with the methods of the current invention, nucleic acid molecules encoding proteins, polypeptides, or peptides with proinflammatory cytokine antagonist activity, or proteins, polypeptides, or peptides with cytokine antagonist activity can be administered to a subject with lower airways inflammatory disease including COPD (e.g., whereby the disorder is prevented, managed, treated or ameliorated by reducing or inhibiting production of NO and expression of iNOS, IL-8, IL-6, IL-1, and/or TNF). Further, nucleic acid molecules encoding derivatives, analogs, fragments or variants of proteins, polypeptides, or peptides with cytokine antagonist activity, or derivatives, analogs, fragments or variants of proteins, polypeptides, or peptides with cytokine antagonist activity can be administered to a subject in need of treatment in accordance with the methods of the invention. Preferably, such derivatives, analogs, variants and fragments retain the cytokine antagonist activity of the full-length, wild-type protein, polypeptide, or peptide.

In another embodiment, agents that are commercially available and known to function as cytokine antagonists are used in the compositions and methods of the invention. The proinflammatory cytokine antagonist activity of an agent can be determined in vitro and/or in vivo by any technique well known to one skilled in the art. However, proteins, polypeptides, or peptides that can be used as proinflammatory cytokine inhibitors can be produced by any technique well known in the art or described herein. Proteins, polypeptides, or peptides with cytokine antagonist activity can be engineered to increase the in vivo half-life of such proteins, polypeptides, or peptides utilizing techniques well known in the art.

Cytokine antagonists and their dosages, routes of administration and recommended usage are known in the art and have been described in such literature as the Physician's Desk Reference (60th ed., 2006). As described in U.S. Pub. App. 20030143603 chimeric antibody cA2 consists of the antigen binding variable region of the high-affinity neutralizing mouse anti-human TNFalpha IgG1 antibody, designated A2, and the constant regions of a human IgG1, kappa immunoglobulin. The human IgG1 Fc region improves allogeneic antibody effector function, increases the circulating serum half-life, and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line. All of which is incorporated in its entirety herein.

In one embodiment, in accordance with efforts to optimize mucosal activity of a neutralizing antibody, a Fab fragment is preferred for topical dosing. Using a Fab fragment minimize epithelial transfer (or systemic uptake) that is largely dependent on the Fc region of IgG1, and minimizes the recruitment of inflammatory cells and complement activation. In addition, monoclonal IgM and IgA antibodies may also be produced that are better tolerated as topical reagents with minimal effector functions and minimizing immunogenicity and maximizing half-life in the tissues.

In one embodiment, the pro-inflammatory cytokine inhibitors is an antibody which has high specificity and affinity for TNF, IL-6, IL-8 or IL-1. Preferred methods for determining monoclonal antibody specificity and affinity by competitive inhibition can be found in Harlow, et al., antibodies: A Laboratory Manual, Cold Spring Harbor Laboratory Press, Cold Spring Harbor, N.Y., 1988; Colligan et al., eds., Current Protocols in Immunology, Greene Publishing Assoc. and Wiley Interscience, New York, (1992-2000); Kozbor et al., (1983) Immunol. Today, 4:72-79; Ausubel et al., eds. Current Protocols in Molecular Biology, Wiley Interscience, New York (1987-2000); and Muller, Meth. Enzymol., 92:589-601 (1983), which are incorporated herein by reference in their entirety.

Numerous additional examples are described in the art of monoclonal proinflammatory cytokine inhibitors including TNF antibodies that can be used in the present invention including but not limited to U.S. Pat. No. 5,231,024; Moller et al. (1990) Cytokine 2(3): 162-169; WO 91/02078; EP 0218868; EP 0288088; Liang et al. (1986) Biochem. Biophys. Res. Comm. 137:847-854; Meager et al. (1987) Hybridoma 6:305-311; Fendly et al. (1987) Hybridoma 6:359-369; Bringman et al. (1987) Hybridoma 6:489-507 (1987); and Hirai et al. (1987) J. Immunol. Meth. 96:57-62; Liang et al. (1986) Biochem. Biophys. Res. Comm. 137: 847-854; Meager, et al. (1987) Hybridoma 6:305-311; Fendly et al. (1987) Hybridoma 6:359-369; Bringman, et al. (1987) Hybridoma 6:489-507 (1987); Hirai et al. (1987) J. Immunol. Meth. 96:57-62 (1987); Moller et al. (1990) Cytokine 2:162-169, all of which are incorporated in their entirety herein by reference.

A preferred embodiment of the present invention is the use of proinflammatory cytokine receptor molecules including those that bind proinflammatory cytokines with high affinity and low immunogenicity (See Schall et al. (1990) Cell 61(2):361-70; Loetscher et al. (1990) Cell 61(2):351-9; and WO 92/07076), which references are entirely incorporated herein by reference. The 55 kDa (p55 TNF-R) and the 75 kDa (p75 TNF-R) TNF cell surface receptors are particularly useful in the present invention. Also useful in the present invention are truncated forms of these receptors, comprising the extracellular domains (ECD) of the receptors or functional portions thereof (Corcoran et al. (1994) Eur. J. Biochem 223(3):831-40). Truncated forms of the TNF receptors, comprising the ECD, have been detected in urine and serum as 30 kDa and 40 kDa TNFalpha Inhibitory binding proteins (Engelmann et al. (1990) J. Biol. Chem. 265(3):1531-6). In yet another preferred embodiment, TNF receptor molecules that can be used in the invention are characterized by their ability to treat subjects for extended periods with good to excellent alleviation of symptoms and low toxicity. Low immunogenicity and/or high affinity, as well as other undefined properties, can contribute to the therapeutic results achieved by treatment with the proinflammatory cytokine inhibitor (e.g., a TNF-alpha inhibitor, an IL-1 inhibitor, an IL-6 inhibitor or an IL-8 inhibitor).

In one embodiment of the proinflammatory cytokine inhibitor is an antisense nucleic acid antisense to IL-1, IL-6, IL-8, TNF or TNF-alpha. In another embodiment, the proinflammatory cytokine inhibitor is a humanized antibody, a chimeric antibody, a monoclonal antibody, a polyclonal antibody or an antibody fragment the binds to IL-1, IL-6, IL-8 or TNF-alpha. In an alternate embodiment, the proinflammatory cytokine inhibitor is an IL-1 receptor antagonist-like molecule such as e.g., IL-Hy1, IL-1Hy2 or IL-1 TRAP. The proinflammatory cytokine inhibitor may be a soluble cytokine receptor protein such as e.g., a soluble TNF receptor protein, a soluble TNF-alpha receptor protein or a soluble IL-1 receptor protein.

Proinflammatory receptor multimeric molecules and proinflammatory cytokine immunoreceptor fusion molecules, and derivatives and fragments or portions thereof, are additional examples of molecules that are useful in the methods and compositions of the present invention. Proinflammatory cytokine receptor multimeric molecules useful in the present invention comprise all or one or more functional portions of the ECD of two or more cytokine receptors linked via one or more polypeptide linkers or other nonpeptide linkers. Examples of multimeric molecules and methods for their production have been described in U.S. Pub. App. 20040009149, the content of which is incorporated herein by reference in its entirety.

A preferred embodiment of the present invention is the use of TNF immunoreceptor fusion molecules useful in the methods and compositions. These fusion molecules comprise at least one portion of one or more immunoglobulin molecules and all or a functional portion of one or more TNF receptors. Immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al. (1991) Eur. J. Immunol. 21(11):2883-6; Ashkenazi et al. (1991) Proc. Natl. Acad. Sci. 88(23):10535-9; Peppel et al. (1991) J. Exp. Med. 174(6):1483-9; Kolls et al. (1994) Proc. Natl. Acad. Sci. 91(1):215-9; Butler et al. (1994) Cytokine 6(6):616-23; Baker et al. (1994) Eur. J. Immunol. 24(9): 2040-8; U.S. Pat. No. 5,447,851 each of which are entirely incorporated herein by reference). Methods for producing immunoreceptor fusion molecules can also be found in U.S. Pat. Nos. 5,116,964 and 5,225,538; and Capon et al. (1989) Nature 337:525-531.

Functional equivalents of IL-8, IL-6, IL-1, and TNF receptor molecules also include modified cytokine receptor molecules that functionally resemble cytokine receptor molecules that can be used in the present invention (e.g., bind the cytokine with high affinity and possess low immunogenicity). A nonlimiting example includes a functional equivalent of TNF receptor molecule can contain a silent codon, or one or more conservative amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., Current Protocols in Molecular Biology, Greene Publishing Assoc. and Wiley-Interscience, New York (1987-2000).

The present invention is further directed in different aspects to the composition where the solutions are comprised of a proinflammatory cytokine inhibitor and amounts of a divalent cation and to the use of these solutions for the treatment of lower airways inflammatory disorders including COPD where the biological activity of the proinflammatory cytokine inhibitor can be exploited in a novel way. The current invention is also directed to methods for the use of such solutions in the preparation of further formulations comprising a proinflammatory cytokine inhibitor such as subjecting said solutions to elevated temperatures, e.g., as in spray-drying techniques to produce pharmaceutically acceptable formulations of a proinflammatory cytokine inhibitor in the form of a respirable proinflammatory cytokine inhibitor-containing powder, suspension or solution that is therapeutically effective when administered into the lower airways of an individual. Further, acidic solutions that inhibit deamidation of the proinflammatory cytokine inhibitor are rendered stable to precipitation when stored at temperatures at or about ambient temperature.

The present invention is further directed to all associated embodiments thereof relating to the preparation and use of a composition comprised of a liquid solutions of proinflammatory cytokine inhibitor, where the proinflammatory cytokine inhibitor is essentially in monomeric form.

The source of divalent cation can be virtually any calcium salt supplied directly or formed in situ from a suitable pharmaceutically acceptable source. Nonlimiting examples of alternative divalent cations can also include calcium, magnesium, zinc, and the like. The divalent cation component of the present liquid composition is generally at a concentration of from about 0.01 mM to about 1 M, and more preferably, from about 1 mM to about 50 mM.

Surfactants may also be used to prevent soluble and insoluble aggregation and/or precipitation of proteins included in the composition. Suitable surfactants include but are not limited to sorbitan trioleate, soya lecithin, and oleic acid. In certain cases, solution aerosols are preferred using solvents such as ethanol. Thus, at least one proinflammatory cytokine inhibitor formulation can also include a surfactant that can reduce or prevent surface-induced aggregation of the inhibitor caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20. Additional agents known in the art can also be included in the composition.

A preferred embodiment of the pharmaceutical composition comprises a second active ingredient selected from a group consisting of an amiloride, an antibiotic, an antihistamine, an anticholinergic, an anti-inflammatory agent, a mucolytic and a steroid.

The composition may also include additional agents such as e.g., an excipient, a buffer, an isotonicity agent, a preservative, a surfactant, and, a divalent cation, preferably, zinc. The composition can also include an excipient, or an agent for stabilization of at least one proinflammatory cytokine inhibitor antibody composition protein, such as e.g., a buffer, a reducing agent, a bulk protein, amino acids (such as e.g., glycine or proline) or a carbohydrate. Bulk proteins useful in formulating at least one proinflammatory cytokine inhibitor composition proteins include albumin. Typical carbohydrates useful in formulating at least one proinflammatory cytokine inhibitor include but are not limited to sucrose, mannitol, lactose, trehalose, or glucose.

The composition herein may contain other components, such as active agents and inactive agents such as excipients, with the only requirements being that such other components are pharmaceutically acceptable and do not interfere with the effect of the proinflammatory cytokine inhibitor, divalent cation or other active and inactive ingredients.

A liquid composition herein can be used as such with a delivery device, or they can be used for the preparation of pharmaceutically acceptable formulations comprising a proinflammatory cytokine inhibitor that are prepared for example by the method of spray drying. The methods of spray freeze-drying proteins for pharmaceutical administration of Maa et al. (2001) Curr. Pharm. Biotechnol. 1(3):283-302, are incorporated herein. In another embodiment of the current invention, the liquid solutions herein are freeze spray dried and the spray-dried product is collected as a dispersible proinflammatory cytokine inhibitor-containing powder that is therapeutically effective when administered into the lower airways of an individual.

The composition is preferably administered to the mammal in a pharmaceutically acceptable carrier. Suitable carriers and their formulations are described in Remington's Pharmaceutical Sciences, 2005, Mack Publishing Co. Typically, an appropriate amount of a pharmaceutically acceptable salt is used in the formulation to render the formulation isotonic. Examples of the pharmaceutically acceptable carrier include liquids such as saline, Ringer's solution and dextrose solution. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of proinflammatory cytokine inhibitor being administered.

Effective dosages and schedules for administering the composition may be determined empirically, and making such determinations is within the skill in the art. Those skilled in the art will understand that the dosage of any composition that must be administered will vary depending on, for example, the mammal which will receive the composition, the route of administration, the particular composition used including the co-administration of other drugs and other drugs being administered to the mammal. A typical daily dosage of the composition used alone might range from about (e.g., 0.25 mg to up to 5.0 mg per oral or nasal inhalation, or 0.125 mg to 2.5 mg per oral or nasal inhalation), however depending on symptoms and body weight a higher or lower dosage may be appropriate.

Alternatively, the dosage administered can vary depending upon known factors, such as the pharmacodynamic characteristics of the particular agent, and its mode and route of administration; age, and health of the recipient; nature and extent of symptoms, kind of concurrent treatment, frequency of treatment, and the effect desired.

As an example, treatment of mammals can be provided as a one-time or periodic dosage of at least one antibody of the present invention 0.01 to 100 mg, such as 0.025, 0.05, 0.075, 0.1, 0.125, 0.25, 0.50, 0.75, 1.0, 1.125, 1.25, 1.5, 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

It will furthermore be appreciated that a therapeutically effective amount of a particular composition can be determined by those of ordinary skill in the art with due consideration of the factors pertinent to the subject.

In one embodiment, a proinflammatory cytokine inhibitor may also be administered along with other active or pharmacologic agents used to treat the conditions listed above, such as UTP, amiloride, antibiotics, anti-histamines, anti-cholinergics, anti-inflammatory agents, and mucolytics (e.g., n-acetyl-cysteine). It may also be useful to administer the proinflammatory cytokine inhibitor along with other therapeutic human proteins including but not limited to serine and other protease inhibitors, gamma-interferon, enkephalinase, nucleases, colony stimulating factors, albumin, and antibodies. Still other compounds may be used in a particular composition such as a surfactant and preservative. The proinflammatory cytokine inhibitor may be administered sequentially or concurrently with the one or more other pharmacologic agents. The amounts of proinflammatory cytokine inhibitor and pharmacologic agent depend, for example, on what type of drugs are used, the type of lower airways inflammatory disorder being treated, and the scheduling and routes of administration. Following administration of proinflammatory cytokine inhibitor to the mammal, the mammal's physiological condition can be monitored in various ways well known to one of ordinary skill in the art.

The present invention further provides compositions for the treatment, prophylaxis, and amelioration of a disorder in a subject. In one embodiment, a composition comprises one, two, three, four or more compounds of the invention, or a pharmaceutically acceptable salt, solvate, or hydrate thereof. In another embodiment, a composition comprises compounds of the invention in the form of a solution that may contain a stabilizing compound(s) and/or a preservative(s). In another embodiment of the invention, bulk-drug compositions (which can be non-sterile) useful in the manufacture of pharmaceutical compositions and in the preparation of unit dosage forms are included.

In another embodiment, the composition used for treating disorders of the lower airways may comprise a proinflammatory cytokine inhibitor and other compounds including but not limited to a mucoregulatory compound, a corticosteroid, a surfactant, an anticholinergic compound, a bronchodilotor, a nuclease, an antibiotic, an antiviral agent, and an antiangiogenic agent.

Preferred salts include, but are not limited, to calcium, magnesium, zinc, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p toluenesulfonate, and pamoate (i.e., 1,1'-methylene bis (2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion.

In one embodiment, the composition is a pharmaceutical composition of single unit or multiple unit dosage forms. Pharmaceutical compositions of single unit or multiple unit dosage forms of the invention comprise a prophylactically or therapeutically effective amount of one or more compositions (e.g., a compound of the invention, or other prophylactic or therapeutic agent), typically, one or more vehicles, carriers, or excipients, stabilizing agents, and/or preservatives. Preferably, the vehicles, carriers, excipients, stabilizing agents and preservatives are pharmaceutically acceptable.

This invention further encompasses anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Suitable vehicles are well known to those skilled in the art of pharmacy, and non-limiting examples of suitable vehicles include glucose, sucrose, starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention further encompasses pharmaceutical compositions and dosage forms that comprise one or more compounds that reduce the rate by which an active ingredient will decay or the composition will change in character. So called "stabilizers" or "preservatives" and may include, but are not limited to, amino acids, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride. Additional nonlimiting examples of amino acids include glycine or proline.

A pharmaceutical composition of the invention is formulated to be compatible with its intended route of administration. Examples of routes of administration within the lower airways include, but are not limited to oral or nasal inhalation (e.g., inhalation of sufficiently small particles to be deposited expressly within the lower airways). In various embodiments, the pharmaceutical compositions or single unit dosage forms are sterile and in suitable form for administration to a subject, preferably an animal subject, more preferably a mammalian subject, and most preferably a human subject.

The composition, shape, and type of dosage forms of the invention will typically vary depending on their use. Nonlimiting examples of dosage forms include powders; solutions; aerosols (e.g., sprays, metered or nonmetered dose atomizers, oral or nasal inhalers including metered dose inhalers (MDI)); liquid dosage forms suitable for mucosal administration to a patient, including suspensions (e.g., aqueous or non-aqueous liquid suspensions, oil-in-water emulsions, or a water-in-oil liquid emulsions), solutions, and sterile solids (e.g., crystalline or amorphous solids) that can also be reconstituted to provide liquid dosage forms suitable for lower airways administration. Formulations in the form of powders or granulates may be prepared using the ingredients mentioned above in a conventional manner using, e.g., a mixer, a fluid bed apparatus or a spray drying equipment.

Generally, a dosage form used in the acute treatment of a disorder may contain larger amounts of one or more of the active ingredients it comprises than a dosage form used in the chronic treatment of the same disease. In addition, the prophylactically and therapeutically effective dosage form may vary among different types of disorders. For example, a therapeutically effective dosage form may contain a compound that has an appropriate antibacterial action when intending to treat a lower airway disorder associated with a bacterial infection. These and other ways in which specific dosage forms encompassed by this invention will vary from one another and will be readily apparent to those skilled in the art. See, e.g., Remington's Pharmaceutical Sciences, 2005, Mack Publishing Co.; Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J. C. Boylan, Marcel Dekker, Inc., New York, 1988, which are incorporated herein by reference in their entirety.

The invention also provides that a pharmaceutical composition can be packaged in a hermetically sealed container such as an ampoule or sachette indicating the quantity. In one embodiment, the pharmaceutical composition can be supplied as a dry sterilized lyophilized powder in a delivery device suitable for administration to the lower airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

The present invention also teaches the stabilization (preventing or minimizing thermally or mechanically induced soluble or insoluble aggregation and/or precipitation of an inhibitor protein) of liquid solutions containing a proinflammatory cytokine inhibitor at neutral pH or less than neutral pH by the use of amino acids including proline or glycine, with or without divalent cations resulting in clear or nearly clear solutions that are stable at room temperature or preferred for pharmaceutical administration.

In one embodiment, one or more compound(s) of the invention or a composition of the invention can be added to an over-the-counter, non-prescriptional medication. Examples of such medication include but are not limited to an analgesic, acetaminophen, non-steroidal anti-inflammatory agent, salicylate, antibiotic, antihistamine, antipruritics, antipyretics, decongestant, expectorant, steroid, zinc and wound care products.

Therapeutic or prophylactic agents include, but are not limited to, plant extracts, small molecules, synthetic drugs, peptides, polypeptides, proteins, nucleic acids (e.g., DNA and RNA nucleotides including, but not limited to, antisense nucleotide sequences, RNAi, sRNAi, triple helices and nucleotide sequences encoding biologically active proteins, polypeptides or peptides), antibodies, synthetic or natural inorganic molecules, mimetic agents, and synthetic or natural organic molecules. In a specific embodiment, a composition comprises one, two, three, four or more compounds of the invention, or a pharmaceutically acceptable salt, solvate, or hydrate thereof, and one, two, three, four or more immunomodulatory agents. In another embodiment, a composition comprises one, two, three, four or more compounds of the invention, or a pharmaceutically acceptable salt, solvate, or hydrate thereof, and one, two, three, four or more anti-angiogenic agents. In yet another embodiment, a composition comprises one, two, three, four or more compounds of the invention, or a pharmaceutically acceptable salt, solvate, or hydrate thereof, and one, two, three, four or more anti-inflammatory agents. In another embodiment, a composition comprises one, two, three, four or more compounds of the invention, or a pharmaceutically acceptable salt, solvate, or hydrate thereof, and one, two, three, four or more anti-cancer agents. In another embodiment, a composition comprises one, two, three, four or more compounds of the invention, or a pharmaceutically acceptable salt, solvate, or hydrate thereof, and one, two, three, four or more anti-viral agents. In another embodiment, a composition comprises one, two, three, four, or more compounds of the invention, or a pharmaceutically acceptable salt, solvate, or hydrate thereof, and one, two, three, four or more one or more antibiotics. In another embodiment, a composition comprising one, two, three, four or more compounds of the invention, or a pharmaceutically acceptable salt, solvate, or hydrate thereof, or one or more natural products, phytochemicals, or botanical extracts. In yet another embodiment, a composition comprises one, two, three, four or more compounds of the invention, or a pharmaceutically acceptable salt, solvate, or hydrate thereof, and any combination of one, two, three, or more of each of the following prophylactic or therapeutic agents: an immunomodulatory agent, an anti-angiogenic agent, a botanical extract, an immunomodulatory agent, an anti-inflammatory agent, an anti-viral agent, or an anti-bacterial agent (e.g., an antibiotic).

Any agent which contributes to the prevention, management, treatment, or amelioration of a disorder (e.g., lower airways inflammatory disorders including COPD) or one or more symptoms thereof can be used in combination with a compound of the invention in accordance with the invention described herein. See, e.g., Gilman et al., Goodman and Gilman's: The Pharmacological Basis of Therapeutics, Tenth Ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W. B. Saunders, Philadelphia, 1996 for information regarding prophylactic or therapeutic agents which have been or are currently being used for preventing, treating, managing, or ameliorating progressive disorders or inflammatory disorders or one or more symptoms thereof. Nonlimiting examples of such agents include anti-inflammatory agents such as corticosteroids (e.g., prednisone and hydrocortisone), glucocorticoids, steroids, non-steriodal anti-inflammatory drugs (e.g., aspirin, ibuprofen, diclofenac, COX-1 and/or COX-2 inhibitors), beta-agonists, anticholinergic agents, mucoregulators (e.g., niflumic acid, talniflumate, MSI-2216) and methyl xanthines), immunomodulatory agents, sulphasalazine, penicillamine, anti-angiogenic agents (e.g., angiostatin), anti-fibrotics, opioids (e.g., morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, beta-prodine, diphenoxylate, fentanil, sufentanil, alfentanil, remifentanil, levorphanol, dextromethorphan, phenazocine, pentazocine, cyclazocine, methadone, isomethadone and propoxyphene), hematopoietic colony stimulating factors (e.g., filgrastim, pegfilgrastim sargramostim, molgramostim and epoetin alfa), antihistamines, anti-viral agents, and antibiotics (e.g., dactinomycin (formerly actinomycin), bleomycin, erythomycin, penicillin, mithramycin, and anthramycin (AMC)).

Additional embodiments of the present invention include methods of preparation of liquid solutions of proinflammatory cytokine inhibitors that are protected from thermally induced aggregation of the inhibitor component of a composition. Chan et al. (1996) Pharm. Res. 13(5):756-61, teaches methods of preparation of DNase solutions to minimize thermal aggregation and the use of calcium to stabilize liquid solutions of DNase, and solutions having neutral or less than neutral pH, all of which are incorporated in their entirety, herein. Surprisingly, similar methods of preparation are relevant to genetically distinct proinflammatory cytokine inhibitors. Additionally, the present invention generally relates to the preparation of liquid solutions of proinflammatory cytokine inhibitors with or without calcium or other divalent cations that are maintained stable at pH less than neutral or neutral. Methods of preparation and their use clinically in the treatment of lower airways disorders susceptible to the biological activity of a proinflammatory cytokine inhibitor, are also discussed in more detail infra.

The present invention also teaches the stabilization (preventing or minimizing thermally or mechanically induced soluble or insoluble aggregation and/or precipitation of an inhibitor protein) of liquid solutions containing a proinflammatory cytokine inhibitor at neutral pH or less than neutral pH by the use of amino acids including proline and glycine, with or without divalent cations resulting in clear or nearly clear solutions that are stable at room temperature or preferred for pharmaceutical administration.

The present invention also incorporates the use of divalent cations as a method of minimizing or inhibiting proinflammatory cytokine inhibitor deamidation of neutral or acidic pH of less than neutral such that deamidation is deterred or inhibited.

Anti-Angiogenic Agents

Anti-angiogenic agents can be used in the compositions and methods of the invention. Non-limiting examples anti-angiogenic agents include proteins, polypeptides, peptides, fusion proteins, antibodies (e.g., human, humanized, chimeric, monoclonal, polyclonal, Fvs, ScFvs, Fab fragments, F(ab)2 fragments, and antigen-binding fragments thereof) such as antibodies that immunospecifically bind to TNF-alpha, nucleic acid molecules (e.g., antisense molecules or triple helices), organic molecules, inorganic molecules, and small molecules that reduce or inhibit angiogenesis. In particular, examples of anti-angiogenic agents, include, but are not limited to, squalamine, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, anti-integrin alpha V beta 3 antibodies, acid fibroblast growth factor (aFGF) antagonists, basic fibroblast growth factor (bFGF) antagonists, vascular endothelial growth factor (VEGF) antagonists (e.g., anti-VEGF antibodies such as Avastin), and VEGF receptor (VEGFR) antagonists (e.g., anti-VEGFR antibodies).

Examples of integrin alpha V beta 3 antagonists include, but are not limited to, proteinaceous agents such as non-catalytic metalloproteinase fragments, RGD peptides, peptide mimetics, fusion proteins, disintegrins or derivatives or analogs thereof, and antibodies that immunospecifically bind to integrin alpha V beta 3, nucleic acid molecules, organic molecules, and inorganic molecules. Non-limiting examples of antibodies that immunospecifically bind to integrin alpha V beta 3 include 11D2 (Searle). Non-limiting examples of small molecule peptidometric integrin alpha V beta 3 antagonists include 5836 (Searle) and 5448 (Searle). Examples of disintegrins include, but are not limited to, Accutin. The invention also encompasses the use of any of the integrin alpha V beta 3 antagonists in the compositions and methods of the invention as described in U.S. Pat. Nos. 5,652,109; 5,652,110; 5,578,704; 5,149,780; 5,196,511; 5,204,445; 5,262,520; 5,306,620; 5,478,725; 5,498,694; 5,523,209; 5,578,704; 5,589,570; 5,652,109; 5,652,110; 5,693,612; 5,705,481; 5,753,230; 5,767,071; 5,770,565; 5,780,426; 5,817,457; 5,830,678; 5,849,692; 5,955,572; 5,985,278; 6,048,861; 6,090,944; 6,096,707; 6,130,231; 6,153,628; 6,160,099; and 6,171,588; and International Publication Nos. WO 95/22543; WO 98/33919; WO 00/78815; WO 00/31248; WO 98/46264; WO 98/40488; and WO 02/070007, each of which is incorporated herein by reference in its entirety.

Cleaved antithrombin was discovered to have potent anti-angiogenic activity (O'Reilly et al. (1999) 285(5435): 1926-8). Accordingly, in one embodiment, an anti-angiogenic agent is the anti-angiogenic form of antithrombin. In another embodiment of the invention, an anti-angiogenic agent is the 40 kDa and/or 29 kDa proteolytic fragment of fibronectin.

Nucleic acid molecules encoding proteins, polypeptides, or peptides with anti-angiogenic activity, or proteins, polypeptides or peptides with anti-angiogenic activity can be administered to a subject with a disorder (e.g., a disorder characterized by or associated with aberrant angiogenesis, a proliferative disorder, an inflammatory disorder or a disorder prevented, managed, treated or ameliorated by inhibiting NF-kappa B activation and phosphorylation of p44/42 MAPK, or by reducing or inhibiting production of NO, IL-1beta, and expression of iNOS and Cox-2 gene expression) in accordance with the methods of the invention. Further, nucleic acid molecules encoding derivatives, analogs, fragments, or variants of proteins, polypeptides, or peptides with anti-angiogenic activity, or derivatives, analogs, fragments, or variants of proteins, polypeptides, or peptides with anti-angiogenic activity can be administered to a subject with a disorder (e.g., a disorder characterized by or associated with aberrant angiogenesis, a proliferative disorder, an inflammatory disorder or a disorder prevented, managed, treated or ameliorated by inhibiting NF-kappa B activation and phosphorylation of p44/42 MAPK, or by reducing or inhibiting production of NO, IL-1beta, and expression of iNOS and Cox-2 gene expression) in accordance with the methods of the invention. Preferably, such derivatives, analogs, variants, and fragments retain the anti-angiogenic activity of the full-length, wild-type protein, polypeptide, or peptide.

Proteins, polypeptides, or peptides that can be used as anti-angiogenic agents can be produced by any technique well known in the art or described herein. Proteins, polypeptides, or peptides with anti-angiogenic activity can be engineered so as to increase the in vivo half-life of such proteins, polypeptides, or peptides utilizing techniques well known in the art or described herein. Preferably, anti-angiogenic agents that are commercially available are used in the compositions and methods of the invention. The anti-angiogenic activity of an agent can be determined in vitro and/or in vivo by any technique well known to one skilled in the art or described herein.

Anti-angiogenic agents and their dosages, routes of administration and recommended usage are known in the art and have been described in such literature as the Physician's Desk Reference (60th ed., 2006).

Anti-Inflammatory Agents

In one embodiment of the invention, the composition further comprises and anti-inflammatory agent. Thus, anti-inflammatory therapy (e.g., an anti-inflammatory agent) can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, antihistamines (e.g., ethanolamines, ethylenediamines, piperazines, and phenothiazine), and methyl xanthines. Examples of NSAIDs include, but are not limited to, aspirin, ibuprofen, salicylates, acetominophen, celecoxib, diclofenac, etodolac, fenoprofen, indomethacin, ketorolac, oxaprozin, nabumentone, sulindac, tolmentin, rofecoxib, naproxen, ketoprofen and nabumetone. Such NSAIDs function by inhibiting a cyclooxgenase enzyme (e.g., COX-1 and/or COX-2). Examples of steroidal anti-inflammatory drugs include, but are not limited to, glucocorticoids, dexamethasone, cortisone, hydrocortisone, prednisone, prednisolone, triamcinolone, azulfidine, and eicosanoids such as prostaglandins, thromboxanes, and leukotrienes.

Anti-inflammatory agents and their dosages, routes of administration and recommended usage are known in the art and have been described in such literature as the Physician's Desk Reference ($60^{th}$ ed., 2006).

Antibiotics

The composition may also further comprise an antibacterial agent and/or antibiotics. Thus, suitable examples of antibacterial agents or antibiotics include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithromycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional nonlimiting examples of antibacterial agents include Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefmetazole; Cefmetazole Sodium; Cefonicid Monosodium; Cefonicid Sodium;

Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Gatifloxacin Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Antibiotics and their dosages, routes of administration and recommended usage are known in the art and have been described in such literature as the Physician's Desk Reference (60$^{th}$ ed., 2006).

Antiviral Agents

In another embodiment, the composition may contain an anti-viral agent. Non-limiting examples of anti-viral agents include proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell.

Many examples of antiviral compounds that can be used in combination with the compounds of the invention are known in the art and include but are not limited to: rifampicin, nucleoside reverse transcriptase inhibitors (e.g., AZT, ddI, ddC, 3TC, d4T), non-nucleoside reverse transcriptase inhibitors (e.g., Efavirenz, Nevirapine), protease inhibitors (e.g., aprenavir, indinavir, ritonavir, and saquinavir), idoxuridine, cidofovir, acyclovir, ganciclovir, zanamivir, amantadine, and Palivizumab. Other examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscamet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin;

Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime, zinc, heparin, anionic polymers.

Antiviral agents and their dosages, routes of administration and recommended usage are known in the art and have been described in such literature as the Physician's Desk Reference (60th ed., 2006).

Antifungal Compounds

In addition, the composition may further contain antifungal compounds. Suitable exemplary antifungal compounds include, but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride. Antifungal agents and their dosages, routes of administration and recommended usage are known in the art and have been described in such literature as the Physician's Desk Reference ($60^{th}$ ed., 2006).

Mucoregulator Compounds

The compositions containing a proinflammatory cytokine inhibitor may further comprise a mucoregulator. Mucoregulator compound downregulate the production of soluble gel-forming mucins in lower airways inflammatory disorders including COPD. These compounds and methods of modulating mucin synthesis and the therapeutic application of compounds in controlling mucin over-production in lower airways inflammatory disorder including COPD are described in U.S. Pat. Nos. 6,737,427; 6,576,434; 6,037,149; and 5,908,839, which are herein incorporated by reference in their entirety.

Molecules that decrease mucin synthesis or levels include analogues and derivatives of anthranilic acid (2-aminobenzoic acid), N-derivatized anthranilic acid, flufenamic acid, derivatives of 2-amino-nicotinic acid, derivative of 2-aminophenylacetic acid, talniflumate, bendroflumethiazide, or a prodrug of any of these compounds. A prodrug is a molecule that is administered in a form other than that described above and is converted in the body of the subject into the form described herein. Preferred prodrugs include, but are not limited to, prodrugs of fenamates. Some preferred prodrugs are esters of the acid form of the molecule that decreases mucin synthesis or levels. Preferred esters include, but are not limited to, esters of NFA, for example, the beta-morpholinoethyl ester, morniflumate, and the phthalidyl ester, talniflumate.

Surfactants

The pharmaceutical compositions and methods according to the invention may further comprise surfactants and spreading agents. In a preferred embodiment, the invention provides formulations that incorporate a surfactant. Surfactants as noted above may be added to improve delivery and/or stability of the composition, minimize heat and agitation induced soluble and insoluble aggregation of proteins, aid rehydration and/or wetting of membranes, and fluidify secretions (Luisetti et al. (1992) Minerva Pediatr. 44(9):427-30; Chou et al. (2005) J. Pharm. Sci. 94(6):1368-81; Webb et al. (2002) J. Pharm. Sci. 91(2):543-58; Webb et al. (2002) J. Pharm. Sci. 91(6):1474-87; Kreilgaard et al. (1998) J. Pharm. Sci. 87(12):1597-603; Mumenthaler et al. (1994) Pharm. Res. 11(1):12-20; Kerwin et al. (1998) 87(9): 1062-8). Surfactants may be used in conjunction with sugars and divalent cations to stabilize and protect the composition. Surfactants may be ionic or nonionic in nature. Exemplary surfactants include surfactant proteins (such as e.g., SP-A, SP-B, SP-C, and SP-D), lucinactant (SURFAXIN) and tyloxapol (SUPERVENT).

Additional non-limiting examples of surfactants include various water-soluble or insoluble sugar esters such as Tween 80 (polysorbate 80), Tween 20, and Span 60 (sorbitan monostearate). Other commercial surfactants that may be incorporated include but are not limited to pulmonary surfactants such as 1,2 Dipalmitoylphosphatidylcholine; 1,2-Dihexadecyl-sn-Glycerophosphocholine; 1,2 Dihexadecyl sn Glycerophosphocholine; Dipalmitoylphosphatidylcholine; Dipalmitoyllecithin; Dipalmitoyl Phosphatidylcholine; Phosphatidylcholine, Dipalmitoyl Dipalmitoylglycerolphosphocholine; 1,2-Dipalmitoyl-Glycerophosphocholine; 1,2 Dipalmitoyl Glycerophosphocholine; Exosurf, Colfoseril palmitate; polyethylene glycol or PEG, 3-(3-hydroxyalkanoyloxy)alkanoic acids, ALKANOL 189-S, ALKANOL 6112, ALKANOLXC, MERPOL, MERPOL DA, MERPOLHCS, MERPOLLFH, MERPOL OJ, MERPOLSE, BL; polyocyalkylene block copolymers. Additional nonionic agents include: BigCHAP; Bis(polyethylene glycol bis[imidazoyl carbonyl]), Powder; Brij 35, Stein-Moore chromatography; Brij 56; Brij 72; Brij 76; Brij92V; Brij 97; Brij 58P; CremophorEL; Decaethylene glycol monododecyl ether; N-Decanoyl-N-methylglucamine; n-Decyl □-D-glucopyranoside; Decyl □-D-maltopyranoside; n-Dodecanoyl-N-methylglucamide; n-Dodecyl □-D-maltoside; n-Dodecyl □-D-maltoside; n-Dodecyl □-D-maltoside; Heptaethylene glycol monodecyl ether; heptaethylene glycol monododecyl ether; Heptaethylene glycol monotetradecyl ether; n-Hexadecyl □-D-maltoside; Hexaethylene glycol monododecyl ether; Hexaethylene glycol monohexadecyl ether; Hexaethylene glycol monooctadecyl ether; Hexaethylene glycol monotetradecyl ether; Igepal CA-630; Methyl-6-O—(N-heptylcarbamoyl)-□-D-glucopyranoside; Nonaethylene glycol monododecyl ether; N-Nonanoyl-N-methylglucamine; N-Nonanoyl-N-methylglucamine; octaethylene glycol monodecyl ether; Octaethylene glycol monododecyl ether;

Octaethylene glycol monohexadecyl ether; Octaethylene glycol monooctadecyl ether; Octaethylene glycol monotetradecyl ether; Octyl-☐-D-glucopyranoside; Pentaethylene glycol monodecyl ether; Pentaethylene glycol monododecyl ether; Pentaethylene glycol monohexadecyl ether; Pentaethylene glycol monohexyl ether, Pentaethylene glycol monooctadecyl ether; Pentaethylene glycol monooctyl ether; Polyethylene glycol diglycidyl ether; Polyethylene glycol ether W-1; Polyoxyethylene 10 tridecyl ether; Polyoxyethylene 100 stearate; Polyoxyethylene 20 isohexadecyl ether; Polyoxyethylene 20 oleyl ether; Polyoxyethylene 40 stearate; Polyoxyethylene 50 stearate; Polyoxyethylene 8 stearate; Polyoxyethylene bis(imidazolyl carbonyl); Polyoxyethylene 25 propylene glycol stearate; Saponin from Quillaja bark; Span 20; span 40; Span60; Span 65; Span 80; Span 85; Tergitol, Type 15-S-12; Tergitol, Type 15-S-30; Tergitol, Type 15-S-5; Tergitol, Type 15-S-7; Tergitol, Type 15-S-9; Tergitol, Type NP-10; Tergitol, Type NP-4; Tergitol, Type NP-40; Tergitol, Type NP-7; Tergitol, Type NP-9; Tergitol, MIN FOAM 1×; Tergitol, MIN FOAM 2×; Tergitol, Type TMN-10; Tergitol, Type TMN-6; Tetradecyl-☐-D-maltoside; Tetraethylene glycol monodecyl ether; Tetraethylene glycol monododecyl ether; Tetraethylene glycol monotetradecyl ether; Triethylene glycol monodecyl ether; Triethylene glycol monododecyl ether; Triethylene glycol monohexadecyl ether; Triethylene glycol monooctyl ether, Liquid; Triethylene glycol monotetradecyl ether; Triton CF-21, Solution; Triton CF-32; Triton DF-12; Triton DF-16; Triton GR-5M; Triton X-100, reduced; Triton X-102; Triton X-15; Triton X-151; Triton X-207; Triton X-100; Triton X-100, Peroxide- and carbonyl-free; TritonX-114; TritonX-165 solution; TritonX-305 solution; Triton X-405 solution; TritonX-45; Triton X-705-70 solution; TWEEN 20, Viscous liquid; TWEEN 20, Low-peroxide; Low-carbonyls; TWEEN 20; TWEEN 20, Low-peroxide; Low-carbonyls; TWEEN 20 solution, 70% in water; TWEEN 20 solution, 10% in water; TWEEN 21; TWEEN 40, Viscous liquid; TWEEN60; TWEEN 61; TWEEN 65; TWEEN80, Viscous liquid; TWEEN 80; TWEEN 80; TWEEN 80, Viscous liquid, Low Peroxide; TWEEN 80, Viscous liquid, Preservative Free, Low-peroxide; Low-carbonyls; TWEEN 80 solution, Low Peroxide, 10% (Solution); TWEEN 80 solution, Liquid; TWEEN 81; TWEEN85; Tyloxapol; Tyloxapol; n-Undecyl ☐-D-glucopyranoside.

Dosage & Frequency of Administration

The amount of the compound or composition of the invention that will be effective in conjunction with a particular method will vary e.g., with the nature and severity of the disorder and the device by which the active ingredient(s) is administered. The frequency and dosage will also vary according to factors specific for each subject, such as age, body, weight, response, and the past medical history of the subject. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (60$^{th}$ ed., 2006).

Exemplary doses include milligram or microgram amounts of the compound of the invention. In general, the recommended daily dose range of a compound of the invention for the conditions described herein lie within the range of from about 0.01 mg to about 100 mg per day, given as a single once-a-day dose preferably or as divided doses throughout a day. In one embodiment, the daily dose is administered twice daily in equally divided doses. Specifically, a daily dose range should be from about 100 micrograms to about 50 milligrams per day, more specifically, between about 500 micrograms and about 5 milligrams per day. In managing the patient, the therapy should be initiated at a lower dose, perhaps about 500 micrograms, and increased if necessary up to about 5.0 milligrams per day as either a single dose or divided doses, depending on the patient's global response. It may be necessary to use dosages of the active ingredient outside the ranges disclosed herein in some cases, as will be apparent to those of ordinary skill in the art. Furthermore, it is noted that in instances where a clinician or treating physician is involved, such a person will know how and when to interrupt, adjust, or terminate therapy in conjunction with individual subject response.

Different therapeutically effective amounts of a specific composition may be applicable for different diseases, as will be readily known by those of skill in the art. Similarly, different therapeutically effective compounds may be included in a specific composition depending on the subject's disease. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a subject is administered multiple dosages of a compound or compositions of the invention, not all of the dosages need be the same. For example, the dosage administered to the subject may be increased to improve the prophylactic or therapeutic effect of the compound or it may be decreased to reduce one or more side effects that a particular subject is experiencing.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, where a physician or clinical visit is involved, two or more therapies (e.g., prophylactic or therapeutic agents) are administered within the same subject visit. The therapies can be administered simultaneously.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing or treating a disorder, (e.g., lower airways inflammatory disorders including COPD, or symptoms thereof) comprising administering to a subject in need thereof a dose of at least 100 micrograms, preferably at least 250 micrograms, at least 500 micrograms, at least 1000 micrograms, at least 5000 micrograms, or more of one or more compounds of the invention once every 3 days, preferably, once every 4 days, once every 5 days, once every 6 days, once every 7 days, once every 8 days, once every 10 days, once every two weeks, once every three weeks, or once a month.

Dosage Forms

The current invention provides for dosage forms comprising a pro-inflammatory inhibitor suitable for treating mucosal tissues within the lower airways The dosage forms can be formulated e.g., as sprays, aerosols, gels, solutions, emulsions, suspensions, nanoparticles, liposomes, or other forms known to one of skill in the art. See e.g., Remington's Pharmaceutical Sciences; Remington: The Science and Practice of Pharmacy supra; Pharmaceutical Dosage Forms and Drug Delivery Systems by Howard C. Ansel et al., Lippincott Williams & Wilkins; 7th edition (Oct. 1, 1999).

Suitable excipients (e.g., carriers and diluents) and other materials that can be used to provide mucosal dosage forms encompassed by this invention are well known to those skilled in the pharmaceutical sciences, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Emulsifying agents, preservatives, antioxidants, gel-forming agents, chelating agents, moisturizers, or humectants can also be added to pharmaceutical compositions and dosage forms if desired. Examples of such additional ingredients are well known in the art. See, e.g., Remington's Pharmaceutical Sciences; Remington: The Science and Practice of Pharmacy; Pharmaceutical Dosage Forms and Drug Delivery Systems, supra.

Examples of emulsifying agents include naturally occurring gums, e.g., gum acacia or gum tragacanth, naturally occurring phosphatides, e.g., soybean lecithin and sorbitan monooleate derivatives. Examples of antioxidants include butylated hydroxy anisole (BHA), ascorbic acid and derivatives thereof, tocopherol and derivatives thereof, butylated hydroxy anisole and cysteine. Examples of preservatives include parabens, such as methyl or propyl p-hydroxybenzoate and benzalkonium chloride. Examples of humectants include glycerin, propylene glycol, sorbitol and urea. Examples of chelating agents include sodium EDTA, citric acid and phosphoric acid. Examples of gel forming agents include Carbopol, cellulose derivatives, bentonite, alginates, gelatin, and polyvinylpyrrolidone.

Examples of rehydrating agents include sorbitan esters of fatty acids (Span), polyethylene glycols, glycerol and condensation products between sorbitan esters of fatty acids.

In a specific embodiment, the invention provides formulations for administration to the lower airways. Typically, the composition comprises an active compound(s) in combination with vehicles or the active compound is incorporated in a suitable carrier system. Pharmaceutically inert vehicles and/or excipients for the preparation of the composition include, e.g., buffering agents such as boric acid or borates, pH adjusting agents to obtain optimal stability or solubility of the active compound, lactose as a carrier, tonicity adjusting agents such as sodium chloride or borates, viscosity adjusting agents such as hydroxypropyl cellulose, methylcellulose, polyvinylpyrrolidone, polyvinyl alcohols or polyacrylamide, oily vehicle such as vehicles comprising *arachis* oil, castor oil and/or mineral oil. Emulsions and suspensions of the active drug substance may also be presented in the composition. In these cases, the composition may furthermore comprise stabilizing, dispersing, wetting, emulsifying and/or suspending agents.

Additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); and urea.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery-enhancing or penetration-enhancing agent. Different salts, hydrates, or solvates of the active ingredients can be used to adjust further the properties of the resulting composition.

Articles of Manufacture

The invention encompasses articles of manufacture. A typical article of manufacture of the invention comprises a unit dosage form of a composition or compound of the invention. In one embodiment, the unit dosage form is a container, preferably a sterile container, containing an effective amount of a composition or compound of the invention and a pharmaceutically acceptable carrier or excipient. The article of manufacture can further comprise a label or printed instructions regarding the use of composition or compound or other informational material that advises the physician, technician, consumer, subject, or patient on how to prevent, treat or derive a beneficial result pertaining to the disorder in question. The article of manufacture can include instructions indicating or suggesting a dosing regimen including, but not limited to, actual doses, monitoring procedures, and other monitoring information. The article of manufacture can also further comprise a unit dosage form of another prophylactic or therapeutic agent, for example, a container containing an effective amount of another prophylactic or therapeutic agent. In a specific embodiment, the article of manufacture comprises a container containing an effective amount of a composition or compound of the invention and a pharmaceutically acceptable carrier or excipient and a container containing an effective amount of another prophylactic or therapeutic agent and a pharmaceutically acceptable carrier or excipient. Examples of other prophylactic or therapeutic agents include, but are not limited to, those listed above. Preferably, the packaging material and container included in the article of manufacture are designed to protect the stability of the product during storage and shipment.

Article of manufacture of the invention can further comprise devices that are useful for administering the unit dosage forms. Examples of such devices include, but are not limited to, syringes, dry powder inhalers, metered dose and nonmetered dose inhalers, and nebulizers.

Articles of manufacture of the invention can further comprise pharmaceutically acceptable vehicles or consumable vehicles that can be used to administer one or more active ingredients (e.g., a compound of the invention). For example, if an active ingredient is provided in a solid form that must be reconstituted for lower airways administration, the article of manufacture can comprise a sealed container of a suitable vehicle in which the active ingredient can be dissolved. For lower airways administration, a particulate-free sterile solution is preferred. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In another embodiment of the invention, articles of manufacture and kits are provided containing materials useful for treating the pathological conditions described herein and associated problems. The article of manufacture comprises a container with a label. Suitable containers include, for example, bottles, vials, and test tubes. The containers may be formed from a variety of materials such as glass or plastic. The container holds a composition having at least one active compound that is effective for treating, for example, COPD, or complications of COPD. The active agent in the composition is a proinflammatory cytokine inhibitor, and the composition may contain one or more active agents. The label on the container indicates that the compositions is used for treating, for example, lower airways inflammatory disorders including COPD, and may indicate directions for in vivo use, such as those described above.

In a preferred embodiment of the invention, articles of manufacture and kits are provided that specifically incorporate an inhaler. The inhaler preferably is effective at delivering a compound or composition of the invention to specific sites within the lower airways, while minimizing drug distribution to the pharynx and upper airways. The delivery device may incorporate certain parts including but not limited to filters, needles, syringes, valves, atomizers, nasal adapters, electronic nebulizers, meters, heating elements, reservoirs, a power source(s); and package inserts with instructions for use.

The kit of the invention comprises the container described above and may also include a second or third container comprising a pharmaceutically acceptable carrier or buffer, dosing reservoir, or a surfactant. It may further include other materials desirable from a commercial and user standpoint, including other buffers, diluents, and a device for delivery expressly to the lower airways incorporating filters, needles, syringes, valves, atomizers; and package inserts with instructions for use.

Delivery Devices

A general aspect of the current invention is the local delivery expressly to the lower airways of the composition and the delivery device that accomplishes said dosing. Delivery devices of the current invention provide methods for the local delivery of the composition whereby one or more pharmacologically active agents or local treatments of the composition may have local effects expressly in the vicinity of the mucosa of the lower airways. The advantages of local therapy for local disease are discussed elsewhere herein.

For pulmonary administration, preferably at least one proinflammatory cytokine inhibitor is delivered in a particle size effective for reaching the lower airways. There are a several desirable features of an inhalation device for administering the proinflammatory cytokine inhibitors and compositions of the present invention. To be specific, delivery by the inhalation device is generally reliable, reproducible, and accurate. The inhalation device can optionally deliver small dry particles, e.g., less than about 10 microns, preferably about 3 to 5 microns, for good respirability, or dry particles with small stokes radius.

According to the invention, at least one proinflammatory cytokine inhibitor can be delivered by any of a variety of inhalation devices known in the art for administration of a therapeutic agent by inhalation. These devices capable of depositing aerosolized formulations in the lower airways of a patient include but are not limited to metered dose inhalers, sprayers, nebulizers, and dry powder generators. Other devices suitable for pulmonary administration of proteins and small molecules, including proinflammatory cytokine inhibitors, are also known in the art. All such devices can use of formulations suitable for the dispensing of proinflammatory cytokine inhibitors in an aerosol. Such aerosols can be comprised of nanoparticles, microparticles, solutions (both aqueous and nonaqueous), or solid particles.

Nebulizers like AERx Aradigm, the Ultravent nebulizer (Mallinckrodt), and the Acorn II nebulizer (Marquest Medical Products) (U.S. Pat. No. 5,404,871, WO 97/22376, entirely incorporated herein by reference), produce aerosols from solutions.

Metered dose inhalers such as e.g., the Ventolin metered dose inhaler, typically use a propellant gas and require actuation during inspiration (See, e.g., WO 94/16970, WO 98/35888).

Suitable dry powder inhalers like Turbuhaler (Astra), Rotahaler (Glaxo), Diskus (Glaxo), Spiros inhaler (Dura/Elan), devices, and the Spinhaler powder inhaler (Fisons), use breath-actuation of a mixed powder (U.S. Pat. No. 4,668,218, EP 237507, WO 97/25086, WO 94/08552, U.S. Pat. No. 5,458,135, WO 94/06498 all of which are herein entirely incorporated by reference). Metered dose inhalers, dry powder inhalers and the like generate small particle aerosols.

These specific examples of commercially available inhalation devices are intended to be a representative of specific devices suitable for the practice of this invention, and are not intended as limiting the scope of the invention. Preferably, a composition comprising at least one proinflammatory cytokine inhibitor is delivered by a dry powder inhaler or a sprayer.

Once more, the composition of the present invention can be administered as a topical spray or powder to the lower airways of a mammal by a delivery device (e.g., oral or nasal inhaler, aerosol generator, oral dry powder inhaler, through a fiberoptic scope, or via syringe during surgical intervention). These numerous drug delivery devices capable of drug distribution to the lower airways can use a liquid, semisolid, and solid composition. Investigators have found the site of deposition in the lower airways and the deposition area depend on several parameters related to the delivery device, such as mode of administration, particle size of the formulation and velocity of the delivered particles. They describe several in vitro and in vivo methods that may be used by one of ordinary skill in the art to study distribution and clearance of therapeutics delivered to the lower airways, all of which is incorporated in its entirety, herein. Thus, any of these devices may be selected for use in the current invention, given one or more advantages for a particular indication, technique, and subject. These delivery devices include but are not limited to devices producing aerosols (metered-dose inhalers (MDIs)), nebulizers and other metered and nonmetered inhalers.

In general, current container-closure system designs for inhalation spray drug products include both premetered and device-metered presentations using mechanical or power assistance and/or energy from patient inspiration for production of the spray plume. Premetered presentations may contain previously measured doses or a dose fraction in some type of units (e.g., single, multiple blisters, or other cavities) that are subsequently inserted into the device during manufacture or by the patient before use. Typical device-metered units have a reservoir containing formulation sufficient for multiple doses that are delivered as metered sprays by the device itself when activated by the patient.

An embodiment of the current invention is the use of a delivery device that is able to distribute the composition expressly to the mucosa of the lower airways in a subject in need of such treatment. In a preferred embodiment of the current invention, the delivery device is able to distribute the composition expressly to the mucosa of the lower airways in a subject in need of such treatment, with a small amount of composition reaching the pharynx and upper airways.

In a still more preferred embodiment of the invention, the delivery device is able to distribute the composition expressly to the mucosa of the lower airways in a subject in need of such treatment, with a minimal amount distributed to the posterior pharynx and the upper airways.

In a most preferred embodiment of the invention, the delivery device is able to distribute the composition expressly to the mucosa of the lower airways in a subject in need of such treatment, with a negligible amount distributed to the posterior pharynx and the upper airways.

The current invention also incorporates multidose metering or nonmetering inhalers that are specially suited for repeated administrations and can provide numerous doses (typically 60 to up to about 130 doses, or more) either with or without stabilizers and preservatives.

Administration of a composition comprised of a proinflammatory cytokine inhibitor as a spray can be produced by forcing a suspension or solution of at least one proinflammatory cytokine inhibitor through a nozzle under pressure. The nozzle size and configuration, the applied pressure, and the liquid feed rate can be chosen to achieve the desired output and particle size to optimize deposition expressly in the lower airways. An electrospray can be produced, for example, by an electric field in connection with a capillary or nozzle feed. Advantageously, particles of at least one proinflammatory cytokine inhibitor composition delivered by a sprayer have a particle size less than about 20 microns, preferably in the range below 10 microns, and most preferably, about 3 to 5 microns, but other particle sizes may be appropriate depending on the device, composition, and subject needs.

Commercially available nebulizers for liquid formulations, including jet nebulizers and ultrasonic nebulizers may also be useful for administration to the lower airways. Liquid formulations may be directly nebulized and lyophilized powder nebulized after reconstitution.

Alternatively, the composition may be aerosolized using a metered dose inhaler, or inhaled as a lyophilized and milled powder. In addition, the liquid formulation of composition may be instilled through a bronchoscope, placed directly into the affected regions.

In one embodiment of the present invention, a proinflammatory cytokine inhibitor may be administered by a metered dose inhaler. The metered-dose inhaler can contain therapeutically active ingredients dissolved or suspended in a propellant, a mixture of propellants, or a mixture of solvents, propellants, and/or other excipients in compact pressurized aerosol dispensers. The MDI may discharge up to several hundred metered doses of the composition. Depending on the composition, each actuation may contain from a few micrograms ($\mu$g) up to milligrams (mg) of the active ingredients delivered in a volume typically between 25 and 100 microliters. In a metered dose inhaler (MDI), a propellant, at least one proinflammatory cytokine inhibitor, and various excipients or other compounds are contained in a canister as a mixture including a liquified compressed gas (propellants). Actuation of the metering valve releases the mixture as an aerosol, preferably containing particles in the size range of less than about 20 microns. More preferred is a particle size range less than about 10 microns. Most preferred is a particle size range below 5 microns. The desired aerosol particle size can be obtained by employing a formulation of antibody composition protein produced by various methods known to those of skill in the art, including jet-milling, spray drying, critical point condensation, or other methods well known to one of ordinary skill in the art.

Compositions of at least one proinflammatory cytokine inhibitor for use with a metered-dose inhaler device can include a finely divided powder containing at least one proinflammatory cytokine inhibitor as a suspension in a non-aqueous medium, for example, suspended in a propellant with the aid of a surfactant or solubilizing agent. The propellant can be any conventional material including but not limited to chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227). Hydrofluorocarbon is a preferred propellant. A surfactant can be chosen to stabilize the at least one proinflammatory cytokine inhibitor as a suspension in the propellant, to protect the active agent against chemical degradation. In some cases, solution aerosols are preferred using solvents such as ethanol for more water-soluble proinflammatory cytokine inhibitors. Additional agents including a protein can also be included in the composition.

One of ordinary skill in the art will recognize that the methods of the current invention can be achieved by lower airways administration of at least one proinflammatory cytokine inhibitor compositions via devices not described herein. The current invention also incorporates unit-dose metering and nonmetering spray devices that are specially suited for single administration. These devices are typically used for acute short-term treatments (i.e., acute exacerbations) and single-dose delivery (i.e., long acting compositions) and can accommodate a liquid, powder, or mixture of both formulations of the composition. However, in certain circumstances, these unit dose devices may be preferred over multidose devices when used repeatedly in a particular way. Such uses may include but are not limited to repeated procedures where a sterile device is preferred.

Another embodiment of the invention provides for a single-dose syringe prefilled with the composition appropriate for treating the lower airways inflammatory disease of the subject. Said prefilled syringe may be sterile or nonsterile and used in dose administration during procedures to a subject in need of lower airways therapy. An example of an application where a syringe is preferred includes, but is not limited to, the distribution of composition through an endoscope. These examples are not intended to be limiting and one skilled in the art will appreciate that other options exist for delivery of the composition expressly to the lower airways and these are incorporated herein.

In one embodiment of the invention, a composition containing one or more therapeutic agents described herein is directly administered to the lower airways. Such administration may be carried out via use of an intrapulmonary aerolizer, which create an aerosol containing the composition and which may be directly installed into the lower airways. Exemplary aerolizers are disclosed in U.S. Pat. Nos. 5,579,578; 6,041,775; 6,029,657; 6,016,800, and 5,594,987 all of which are herein incorporated by reference in their entirety. Such aerolizers are small enough in size so they can be inserted directly into the lower airways, for example into an endotracheal tube or even into the trachea. In one embodiment, the aerolizer may be positioned near the carina, or first bifurcation, of the lung. In another embodiment, the aerolizer is positioned so as to target a specific area of the lung, for example an individual bronchus, bronchiole, or lobe. Since the spray of the device is directly introduced into the lungs, losses due to deposition of the aerosol due to deposition on the walls of the nasal passages, mouth, throat, and trachea are avoided. Optimally, the droplet size produced by such suitable aerolizer is somewhat larger than those produced by ultrasonic nebulizers. Therefore, the droplets are less likely to be exhaled and thus leading to a delivery efficiency of virtually 100%. In addition, the delivery of the compositions has a highly uniform pattern of distribution.

In one embodiment, such an intrapulmonary aerolizer comprises an aerolizer attached to a pressure generator for delivery of liquid as an aerosol and which can be positioned in close proximity to the lungs by being inserted into the trachea directly or into an endotracheal tube or bronchoscope positioned within the trachea. Such an aerolizer may operate at pressures of up to about 2000 psi and produces particles with a medium particle size of 12 $\square$m.

In an alternate embodiment, such an intrapulmonary aerolizer comprises a substantially elongated sleeve member, a substantially elongated insert, and a substantially elongated body member. The sleeve member includes a threaded inner surface, which is adapted to receive the insert, which is a correspondingly threaded member. The threaded insert provides a substantially helical channel. The body member includes a cavity on its first end, which terminates by an end wall at its second end. The end wall includes an orifice extending therethrough. The body member is connected with the sleeve member to provide the aerolizer of the present invention. The aerolizer is sized to accommodate insertion into the trachea of a subject for administration of compositions containing one or more proinflammatory cytokine inhibitor. For operation of the device, the aerolizer is connected by a suitable tube with a liquid pressure driver apparatus. The liquid pressure driver apparatus is adapted to pass liquid material (e.g., a composition containing one or more proinflammatory cytokine inhibitor) therefrom which is sprayed from the aerolizer. Due to the location of the device deep within the trachea, the liquid material is sprayed in close proximity to the lungs, with resulting improved penetration and distribution of the sprayed material in the lungs.

In an alternate embodiment, such an aerolizer, sized for intratracheal insertion, is adapted for spraying a composition containing one or more proinflammatory cytokine inhibitors directly into the lower airways (e.g., in close proximity to the lungs). The aerolizer is placed into connection with a liquid pressure driver apparatus for delivering of the liquid composition. The aerolizer comprises a generally elongated sleeve member, which defines a first end and a second end and includes a longitudinally extending opening therethrough. The first end of the sleeve member is placed in connection with the liquid pressure driver apparatus. A generally elongated insert is also provided. The generally elongated insert defines a first end and a second end and is received within at least a portion of the longitudinally extending opening of the sleeve member. The insert includes an outer surface which has at least one substantially helical channel provided surrounding its outer surface which extends from the first end to the second end. The substantially helical channel of the insert is adapted to pass the liquid material, which is received by the sleeve member. A generally elongated body member is also included which is in connection with the sleeve member. The body member includes a cavity provided in its first end, which terminates at an end wall which is adjacent its second end. The end wall is provided having an orifice therein for spraying the liquid material, which is received from the insert. The portions of the sleeve member, insert and body member, in combination, are of sufficient size to allow for intratracheal insertion. A method of using such an aerolizer includes the steps of connecting an aerolizer with a first end of a hollow tube member and connecting the second end of the hollow tube member with the liquid pressure driver apparatus. The method further includes the steps of providing the aerolizer in the trachea or into a member which is provided in the trachea, and then activating the liquid pressure driver apparatus for spraying a composition containing one or more proinflammatory cytokine inhibitors therefrom.

In an alternate embodiment, a powder dose composition containing one or more proinflammatory cytokine inhibitors is directly administered to the lower airways via use of a powder dispenser. Exemplary powder dispensers are disclosed in U.S. Pat. Nos. 5,513,630, 5,570,686 and 5,542,412, all of which are herein incorporated in their entirety. Such a powder dispenser is adapted to be brought into connection with an actuator, which introduces an amount of a gas for dispensing the powder dose. The dispenser includes a chamber for receiving the powder dose and a valve for permitting passage of the powder dose only when the actuator introduces the gas into the dispenser. The powder dose is passed from the dispenser via a tube to the lower airways of the subject. The powder dose may be delivered intratracheally, near the carina, which bypasses the potential for large losses of the powder dose to e.g., the mouth, throat, and trachea. In addition, in operation the gas passed from the actuator serves to slightly insufflate the lungs, which provides increased powder penetration. For the intratracheal insertion, the tube can be effected through an endotracheal tube in anesthetized, ventilated subjects, including animal or human patients, or in conscious subjects, the tube be inserted directly into the trachea preferably using a small dose of local anesthetic to the throat and/or a small amount of anesthetic on the tip of the tube, in order to minimize a "gag" response.

In one embodiment, a composition containing one or more therapeutic agents described herein is directly administered to the lower airways. Such administration may be carried out via use of an aerolizer, which create an aerosol containing the composition and which may be directly installed into the lower airways. Exemplary aerolizers are disclosed in U.S. Pat. Nos. 5,579,758; 6,041,775; 6,029,657; 6,016,800; 5,606,789; and 5,594,987 all of which are herein incorporated by reference in their entirety. The invention thus provides for the methods of administering compositions containing one or more proinflammatory cytokine inhibitors directly to the lower airways by an aerolizer.

In particular, an embodiment of the present invention is a new use for the "intratracheal aerosolizer" device which methodology involves the generation of a fine aerosol at the tip of a long, relatively thin tube that is suitable for insertion into the trachea. Thus, the present invention provides a new method of use for this aerosolizer technology in a microcatheter as adapted herein, for use in the lower airways in the prevention, treatment, and care of lower airways disorders including COPD.

In another embodiment of the invention, an aerosolizing microcatheter is used to administer a composition containing a pro-inflammatory cytokine inhibitor. Examples of such catheters and their use, termed "intratracheal aerosolization," which involves the generation of a fine aerosol at the tip of a long, relatively thin tube that is suitable for insertion into the trachea, are disclosed in U.S. Pat. Nos. 5,579,758; 5,594,987; 5,606,789; 6,016,800; and 6,041,775.

In a further embodiment of the present invention is a new use for the microcatheter aerosolizer device (U.S. Pat. Nos. 6,016,800 and 6,029,657) adapted for nasal and paranasal sinus delivery and uses to deliver bioactive agents in the treatment, prevention, and diagnosis of lower airways disorders. One advantage of this microcatheter aerosolizer is the potential small size (0.014" in diameter), and thus capable of being easily inserted into the working channel of a human flexible (1 to 2 mm in diameter) or ridged endoscope and thereby directed partially or completely into the ostium of a paranasal sinus.

One of ordinary skill in the art will recognize that the methods of the current invention can be achieved by lower airway administration of at least one proinflammatory cytokine inhibitor composition via devices not described herein.

Uses of the Compositions and Compounds of the Invention

The present invention provides methods for preventing, managing, treating, or ameliorating a disorder (e.g., inflammatory disorders of the lower airways including COPD) using a compound or composition of the invention in combination with another modality, such as a prophylactic or therapeutic agent known to be useful for, or having been or currently being used in the prevention, treatment, management, or amelioration of a disorder or used in the lessening of discomfort or pain associated with a disorder. Depending on the manner of use of the compositions or compounds, the invention can be co-administered with another modality, or the compositions or compounds of the invention can be mixed and then administered as a single composition to a subject. It is of course contemplated that the methods of the invention can be employed in combination with still other therapeutic uses such as surgical resection and lung transplantation.

In the methods, a composition is administered to a mammal diagnosed as having inflammatory disorders of the lower airways including COPD. It is of course contemplated that the methods of the invention can be employed in combination with still other therapeutic techniques such as endoscopic monitoring and treatment techniques, surgical resection and lung transplantation.

Described herein are uses of the compounds and compositions of the invention for attaining a beneficial effect pertaining to lower airways inflammatory disorders including COPD, providing a beneficial effect pertaining to such disorders, or one or more symptoms thereof. The methods comprise administering to a subject in need thereof a prophylactically or therapeutically effective amount of, one or more compounds or a composition(s) of the invention. For example, administration of such compounds can be via one or more of the pharmaceutical compositions of the invention. It is of course contemplated that the methods of the invention can be employed in combination with oral or nasal inhalation devices. Importantly, it is contemplated that the methods of the invention can be employed in combination with the subcutaneous or intravenous injection, or other systemic routes of administration of proinflammatory cytokine inhibitors. However, still other therapeutic techniques such as endoscopic procedures and treatment techniques, surgical resection and lung transplantation are all included herein.

In one embodiment, a subject in need of prevention, treatment, management, or amelioration of a disorder or a symptom thereof is a subject that has the disorder, that is known to be at risk of the disorder, has been diagnosed with the disorder, has previously recovered from the disorder, or is resistant to current therapy. In particular embodiments, the subject is an animal, preferably a mammal, and more preferably a human, that is predisposed and/or at risk because of a genetic factor(s), an environmental factor(s), or a combination thereof to develop the disorder. In yet another embodiment, the subject is refractory or non-responsive to one or more other treatments for a disorder. In yet another embodiment, the subject is an immunocompromised or immunosuppressed mammal, such as a human.

As used herein, the terms "subject" and "patient" are used interchangeably herein. The terms "subject" and "subjects" refer to an animal, preferably a mammal including a non-primate and a primate (e.g., a monkey such as a cynomolgous monkey, a chimpanzee, and a human), and more preferably a human. The term "animal" also includes, but is not limited to, companion animals such as cats and dogs; zoo animals; wild animals; farm or sport animals such as ruminants, non-ruminants, livestock and fowl (e.g., horses, cattle, sheep, pigs, turkeys, ducks, and chickens); and laboratory animals, such as rodents (e.g., mice, rats), rabbits, and guinea pigs, as well as animals that are cloned or modified, either genetically or otherwise (e.g., transgenic animals).

As used herein, the terms "non-responsive" and "refractory" describe patients treated with a currently available modality (e.g., a prophylactic or therapeutic agent) for a disorder, which is not clinically adequate to relieve one or more symptoms associated with such disorder. Typically, such patients require additional therapy to ameliorate the symptoms associated with their disorder.

As used herein, the terms "modality", modalities", "therapies" and "therapy" can refer to any protocol(s), method(s), and/or agent(s) that can be used in the prevention, treatment, management, or amelioration of a disorder or one or more symptoms thereof. In certain embodiments, the terms "modality", modalities", "therapy" and "therapies" refer to chemotherapy, surgery, biological therapy, immunotherapy and/or other therapies useful in the prevention, management, treatment or amelioration of a disorder or one or more symptoms thereof.

As used herein, the terms "treat," "treatment" and "treating" refer to the reduction or amelioration of the progression, severity and/or duration of a disorder, or the amelioration of one or more symptoms thereof resulting from the administration of one or more modalities (e.g., one or more therapeutic agents such as a compound or composition of the invention).

As used herein, the terms "prevent," "preventing" and "prevention" refer to the prevention or inhibiting of the recurrence, onset, or development of a disorder or a symptom thereof in a subject resulting from the administration of a therapy (e.g., a prophylactic or therapeutic agent), or the administration of a combination of therapies (e.g., a combination of prophylactic or therapeutic agents).

As used herein, the terms "manage," "managing," and "management" refer to the beneficial effects that a subject derives from a therapy (e.g., a prophylactic or therapeutic agent), while not resulting in a cure of the disease. In certain embodiments, a subject is administered one or more modalities (e.g., one or more prophylactic or therapeutic agents) to "manage" a disease so as to prevent the progression or worsening of the disease. In certain embodiments, the method provides a beneficial effect by lessening the discomfort associated with a disorder.

As used herein, the term "therapeutically effective amount" or "effective amount" refers to that amount of a therapeutic agent sufficient to result in the amelioration of one or more symptoms of a disorder, prevent advancement of a disorder, cause regression of a disorder, prevent the recurrence of a disorder, or enhance or improve the prophylactic or therapeutic effect(s) of another modality, or lessen the discomfort associated with a disorder.

As used herein, the terms "therapeutic agent" and "therapeutic agents" refer to any agent(s), which can be used in the treatment, management, or amelioration of a disorder, or one or more symptoms thereof. In certain embodiments, the term "therapeutic agent" refers to a compound or composition of the invention.

As used herein, the terms "prophylactic agent" and "prophylactic agents" as used refer to any agent(s) that can be used in the prevention of a disorder or one or more symptoms thereof. In certain embodiments, the term "prophylactic agent" refers to a compound or composition of the invention. Prophylactic agents may be characterized as different agents based upon one or more effects that the agents have in vitro and/or in vivo.

As used herein, the phrase "prophylactically effective amount" refers to the amount of a prophylactic agent that is sufficient to result in the prevention or inhibition of the development, recurrence, or onset of a disorder or a symptom thereof, or to enhance or improve the prophylactic effect(s) of another modality (e.g., another prophylactic agent).

As used herein, the term "in combination" or "co-administration" refers to the use of more than one modalities (e.g., one or more prophylactic and/or therapeutic agents). The use of the term "in combination" or "co-administration" does not restrict the order in which modalities are administered to a subject with lower airways inflammatory disorders including COPD.

As used herein, the term "synergistic" refers to a combination of compounds of the invention and/or a combination of a compound, compounds or a composition of the invention and another modality (e.g., a prophylactic or therapeutic agent), including one which has been or is currently being used to prevent, manage or treat a disorder, which in combination is more effective than the additive effects of the individual compounds or therapies.

In another embodiment, for the treatment of inflammation, an "effective amount" refers to the amount of a therapy (e.g., a therapeutic agent) that reduces the inflammation of the lower airways or a region of the lower airways (e.g., small airways, bronchi, and trachea).

The following parameters can be used to evaluate the disease course and effects of therapy including but not limited to subjective clinical signs and symptoms (shortness of breath, exercise capacity, chest pain, cough, fever, sputum production), X-ray photographs (either full or limited) computerized axial tomograms (CT) scans and/or magnetic resonance imaging (MRI) of the chest, and cytokine levels (IL-1beta, IL-8 (where available), IL-6, and TNF-alpha) by enzyme-linked immunosorbent assays appropriate for the mammal being evaluated and treated.

Therapeutic agents may be characterized as different agents based upon one or more effects the agents have in vivo and/or in vitro, for example, an anti-inflammatory agent may also be characterized as an immunomodulatory agent.

Preferably, a therapeutically effective amount of a therapy (e.g., a therapeutic agent) reduces the inflammation by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline. Examples of therapeutically effective amounts of compounds are provided infra.

The invention also provides methods for the prevention, treatment, management, or amelioration of progressive disorders or inflammatory disorders, or one or more symptoms thereof, said methods comprising administering to a subject in need thereof a prophylactically or therapeutically effective amount of one or more compounds or a composition of the invention and a prophylactically or therapeutically effective amount of at least one other modality (e.g., at least one other prophylactic or therapeutic agent) other than a compound of the invention.

A first modality (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second modality (e.g., a prophylactic or therapeutic agent such as an anti-inflammatory agent or anti-angiogenic agent) to a subject with lower airways inflammatory disorder including COPD.

A synergistic effect of a combination of modalities (e.g., a combination of prophylactic or therapeutic agents) can permit the use of lower dosages of one or more of the modalities and/or less frequent administration of said modalities to a subject with a disorder. The ability to utilize lower dosages of prophylactic or therapeutic agent and/or to administer said agent less frequently can reduce the toxicity associated with the administration of said agent to a subject without reducing the efficacy of said agent in the prevention, management, or treatment of a disorder. In addition, a synergistic effect can result in improved efficacy of agents in the prevention, management or treatment of a disorder. Moreover, a synergistic effect of a combination of prophylactic or therapeutic agents can avoid or reduce adverse or unwanted side effects associated with the use of either therapy alone.

Side effects are always unwanted, but unwanted effects are not necessarily adverse. An adverse effect might be harmful, uncomfortable or risky. Side effects include, but are not limited to cough, bronchospasm, anaphylaxis, shortness of breath, sinus congestions, sinusitis, pain, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra pyramidal symptoms, akathisia, cardiovascular disturbances and sexual dysfunction.

Inflammatory Disorders

One or more compounds and/or compositions of the invention can be used to prevent, treat, manage, relieve, or ameliorate an inflammatory disorder of the lower airways or one or more symptoms thereof. The compounds of the invention (e.g., proinflammatory cytokine inhibitors) or compositions comprising said compounds may also be administered in combination with one or more other therapies (e.g., one or more other prophylactic or therapeutic agents) useful for the prevention, treatment, management, or amelioration of a condition associated with inflammation (in particular, an inflammatory disorder) or one or more symptoms thereof.

The compounds or compositions of the invention can be used to prevent, reduce, or eliminate one or more symptoms and/or conditions associated with inflammation, for examples, redness, excess warmth, edema (swelling), and/or pain associated with inflammation can be prevented, reduced, or eliminated.

In a specific embodiment, the invention provides a method of preventing, treating, managing, or ameliorating an lower airways disorder associated with inflammation or one or more symptoms thereof, said method comprising contacting with or administering to a subject in need thereof a dose of a prophylactically or therapeutically effective amount of one or more compounds of the invention.

The invention provides methods for preventing, managing, treating or ameliorating an lower airways inflammatory disorders such as COPD, or one or more symptoms thereof in a subject refractory to conventional therapies (e.g., steroids, nonsteroidal anti-inflammatory compounds, anti-cholinergics, mucolytics, nucleases, or antibiotics) for said condition, said methods comprising administering to said subject a dose of a prophylactically or therapeutically effective amount of one or more compounds of the invention. The invention also provides methods for preventing, treating, managing, or ameliorating of lower airways disease or one or more symptoms thereof in a subject refractory to existing single agent therapies for such a condition, said methods comprising administering to said subject a dose of a prophylactically or therapeutically effective amount of one or more compounds of the invention and a dose of a prophylactically or therapeutically effective amount of one or more other therapies (e.g., one or more other prophylactic or therapeutic agents). The invention also provides methods for administering one or more compounds of the invention in combination with any other therapy(ies) to patients who have proven refractory to other treatments but are no longer on this therapy(ies). The invention also provides alternative methods for the prevention, treatment, management, or amelioration of lower airways disease where another therapy has proven or may prove too toxic, i.e., results in unacceptable or unbearable side effects, for the subject being treated. Further, the invention provides methods for preventing a recurrent lower airways inflammatory disorder in patients that have been treated and have no disease activity by administering one or more compounds of the invention.

In a specific embodiment, an effective amount of one or more compounds of the invention is administered to a subject in combination with an effective amount of one or more therapies (e.g., prophylactic or therapeutic agents) useful in preventing, treating, managing, or ameliorating lower airways inflammation, or one or more symptoms thereof. Non-limiting examples of such therapies include, but are not limited to, adrenergic stimulants (e.g., catecholamines) (e.g., epinephrine, isoproterenol, and isoetharine), resorcinols (e.g., metaproterenol, terbutaline, and fenoterol), saligenins (e.g., salbutamol), anticholinergics (e.g., atropine sulfate, atropine methylnitrate, and ipratropium bromide), beta2-agonists, bitolterol, levalbuterol, metaprotereno, pirbuterol, terbutlaine, albuterol, formoterol, and salmeterol), corticosteroids, prednisone, and prednisolone, glucocorticoids (e.g., oral steroids or other systemic or oral steroids, and inhaled gucocoritcoids), other steroids, immunosuppressant agents (e.g., methotrexate and gold salts), leukotriene modifiers (e.g., montelukast, zafirlukast, and zileuton), mast cell stabilizers (e.g., cromolyn sodium and nedocromil sodium), methylxanthines (e.g., theophylline), and mucolytic agents (e.g., acetylcysteine).

In a specific embodiment, an effective amount of a proinflammatory cytokine inhibitor of the invention are administered to the lower airways of a subject in need of such treatment in combination with an effective amount of one or more therapies (e.g., prophylactic or therapeutic agents) useful in preventing, treating, managing, or ameliorating one or more symptoms of a disorder. Non-limiting examples of therapies include antimediator drugs including but not limited to antihistamines, corticosteroids, decongestants, sympathomimetic drugs (e.g., alpha-adrenergic and beta-adrenergic drugs), theophylline and its derivatives, glucocorticoids, and immunotherapies.

In a specific embodiment, an effective amount of a proinflammatory cytokine inhibitor and one or more compounds of the invention are administered to the lower airways of a subject in combination with an effective amount of one or more therapies (e.g., prophylactic or therapeutic agents) useful in preventing, treating, managing, or ameliorating an inflammatory disorder of the lower airways including COPD due to various etiologic agents. Non-limiting examples of such therapies include, but are not limited to, exogenous alpha1anti trypsin or other serine protease inhibitors, antibiotics, anti-cholinergics, mucolytics, nucleases, or yearly influenza vaccine or pneumococcal vaccination.

Infectious Diseases

One or more compounds or compositions of the invention can be used to prevent, treat, manage, relieve, or ameliorate an infectious disease or one or more symptoms thereof. The compounds or compositions of the invention can also be administered in combination with one or more other therapies (e.g., one or more other prophylactic or therapeutic agents) useful for the prevention, treatment, management, or amelioration of a condition associated with an infectious disease or one or more symptoms thereof.

Infectious viruses of mammals and both human and non-human vertebrates, include bacterial, atypical bacteria, retroviruses, RNA viruses and DNA viruses. Examples of virus that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picomaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Retroviruses that are contemplated include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Retroviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picomaviridae, including the genus Enterovirus, poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever, virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, *Herpes saimiri*, Herpesvirus *ateles*, Herpesvirus *sylvilagus*, guinea pig herpes virus, Lucke tumor virus); the family Adenoviridae, including the genus Mastadenovirus (Human subgroups A, B, C, D, E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses that do not fit into the above families such as Kuru and Creutzfeldt-Jacob disease viruses and chronic infectious neuropathic agents.

Bacterial infections or diseases that can be treated or prevented by the methods of the present invention are caused by bacteria including, but not limited to, bacteria that have an intracellular stage in its life cycle, such as mycobacteria (e.g., Mycobacteria *tuberculosis, M. bovis, M. avium, M. leprae*, or *M. africanum*), *rickettsia, mycoplasma, chlamydia*, and *legionella*. Other examples of bacterial infections contemplated include but are not limited to infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio,* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, *Neisseria* species. Specific examples of infectious bacteria include but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Corynebacterium diphtheriae, Erysipelothrix rhusiopathiae, Clostridium perfringens, Clostridium tetani, Enterobacter aerogenes, Klebsiella pneumoniae, Pasteurella multocida, Fusobacterium nucleatum, Streptobacillus moniliformis, Treponema pallidium, Treponema pertenue, Leptospira, Rickettsia*, and *Actinomyces israelli*.

Biological Assays

Aspects of the pharmaceutical compositions or compounds of the invention can routinely be tested in vitro, in a cell culture system, and/or in an animal model organism, such as a rodent animal model system, for a desired activity prior to use in humans. For example, assays can include cell culture assays in which a tissue sample is grown in culture, and exposed to or otherwise contacted with a pharmaceutical composition, and the effect of such composition upon the tissue sample is observed. The tissue sample, for example, can be obtained by collection from a subject. This test allows the identification of the therapeutically most effective therapy (e.g., prophylactic or therapeutic agent(s)) for each individual patient. In various specific embodiments, in vitro assays can be carried out with representative cells of cell types involved in a disorder (e.g., epithelial cells, immune cells, or polyps), to determine if a compound or composition of the invention has a desired effect upon such cell types. As an alternative to the use of tissue, tissue samples, or cell lines, e.g., cancer cell lines can be used in in vitro assays.

The pharmaceutical compositions and compounds of the invention can also be assayed for their ability to induce the expression and/or activation of a gene product (e.g., cellular protein or RNA) and/or to induce signal transduction in immune cells, cancer cells, and/or endothelial cells. The induction of the expression or activation of a gene product or the induction of signal transduction pathways in immune cells and/or epithelial cells can be assayed by techniques known to those of skill in the art including, e.g., ELISA, flow cytometry, northern blot analysis, western blot analysis, RT-PCR kinase assays and electrophoretic mobility shift assays. The compositions and compounds of the invention can also be assayed for their ability to modulate cell proliferation including immune cells using the example, techniques known to those in art, including, but not limited to, tritiated thymidine incorporation, trypan blue cell counts, and fluorescence activated cell sorting ("FACS") analysis. The compositions and compounds of the invention can also be assayed for their ability to induce cytolysis. The compositions and compounds of the invention can also be assayed for their ability to inhibit cell migration, cell adhesion and angiogenesis using techniques well-known to one of skill in the art or as incorporated or described herein.

The pharmaceutical compositions and compounds of the invention can also be tested in suitable animal model systems prior to use in humans. Any animal system well known in the art may be used. In a specific embodiment of the invention, the pharmaceutical compositions and compounds of the invention are tested in a mouse model system. In a preferred embodiment, the mouse is a transgenic animal with a genetic predisposition to environmentally induced lower airways disorders. Such animal model systems include, but are not limited to, rats, mice, chicken, cows, monkeys, pigs, dogs, rabbits, etc. Such model systems are widely used and well known to the skilled artisan.

The data obtained from the cell culture assays and animal studies can be used in formulating a range of dosage of the pharmaceutical compositions and compounds of the invention for use in humans. The dosage of such agents lies preferably within a range with little or no toxicity. The dosage may vary within this range depending upon the dosage form employed and the method of administration utilized. For any agent used in the methods of the invention, the therapeutically effective dose can be estimated initially from cell culture assays. A dose may be confirmed in animal models. Such information can be used to more accurately determine useful doses in humans. Levels in plasma may be measured for systemic absorption, for example, by high performance liquid chromatography (HPLC) and radioimmunoassay (RIA).

Efficacy in preventing or treating a progressive disorder such as COPD may be demonstrated, e.g., by detecting the ability of the pharmaceutical compositions and compounds of the invention to reduce one or more symptoms of the progressive disorder, to reduce the numbers of inflammatory cells, to reduce the spread of inflammatory cells, or to reduce the loss of lung functions, as for example, by using techniques and methods described herein.

Without further description, it is believed that one of ordinary skill in the art can, using the proceeding description and the following illustrative examples, make and utilize the compounds of the present invention and practice the claimed methods. The invention will be more fully understood by reference to the following examples. The following examples therefore, specifically point out preferred embodiments of the present invention, and are not to be construed as limiting in anyway the remainder of the disclosure.

EXAMPLES

Example 1

Assessing the Safety, Pharmacological and Biochemical Effects of Nebulized Anakinra in Healthy Smokers An exploratory, single-dose, dose-escalating phase I study was performed with 18 healthy smokers. All 18 subjects received nebulized inhalation of anakinra. The subjects were separated into three (3) dose groups, and dosage forms of anakinra were administered as follows: six (6) subjects received a dosage level of 0.75 mg, six (6) subjects received a dosage level of 3.75 mg, and six (6) subjects received a dosage level of 7 mg. There was a 14-day interval between each successive dose group whereby the safety of four (4) subjects in the prior dose group was assessed. Safety assessment included physical examinations, vital sign measurements, clinical laboratory evaluations, documentation of AEs, electrocardiogram (ECG) assessments, and pulmonary function ($FEV_1$), forced expiratory flow (FEF) of 25-75%, and forced vital capacity (FVC). Bronchoscopy for pharmacologic and biochemical endpoint was performed on two (2) subjects within each dose group, after the four (4) subjects in each dose group were analyzed for safety. Bronchoscopic analysis was carried out independent of the safety analysis. The total duration of the study was 2.5 months.

Example 2

Assessing the Safety and Efficacy of Nebulized Anakinra in Subjects with Cystic Fibrosis A double-blind, randomized, placebo-controlled, multiple-dose, phase II study was performed with 180 subjects diagnosed with cystic fibrosis. One hundred and thirty-five (135) subjects received nebulized inhalation of anakinra and forty-five (45) subjects received placebo as control. The subjects were separated into four (4) dose groups. Dosage forms of anakinra were administered as follows: forty-five (45) subjects received a dosage level of 0.75 mg, forty-five (45) subjects received a dosage level of 3.75 mg and forty-five (45) subjects received a dosage level of 7.5 mg; the fourth group of forty-five (45) subjects, received placebo as a control. The study medication is administered once daily for 6 months. Drug efficacy is determined by measuring from the baseline, the: time of the first exacerbation and the number of pulmonary exacerbations, change in spirometric measurement of forced expiratory volume in one second ($FEV_1$), change in health-related quality of life determined from the cystic fibrosis quality of life (CFQOL) questionnaire, cumulative incidence of the use of intravenous (IV) antibiotics, number of hospitalizations and number of days hospitalized, change in computed tomography (CT) imaging and the change in neutrophil elastase and bacterial counts in induced sputum. Safety assessment included acute respiratory illness checklist (ARIC) score, gastrointestinal (GI) tolerability, use of IV antibiotics, number of hospitalizations, CT imaging, change in bacterial counts, physical examinations, vital sign measurements, clinical laboratory evaluations, documentations of AEs, and electrocardiogram (ECG) assessments. The total duration of the study is 16 months.

Example 3

Assessing the Safety and Efficacy of Nebulized Anakinra in Subjects with Bronchiolitis Obliterans A double-blind, randomized, placebo-controlled, multiple-dose, phase II study was performed with 45 cystic fibrosis subjects diagnosed with bronchiolitis obliterans. Thirty (30) subjects receive nebulized inhalation of anakinra and fifteen (15) subjects received placebo as control. The subjects are separated into three (3) dose groups. Dosage forms of anakinra are administered as follows: fifteen (15) subjects received a dosage level of 3.75 mg and fifteen (15) subjects received a dosage level of 7.5 mg; the third group of fifteen (15) subjects, received placebo as a control. The study medication is administered once daily for six (6) months. Drug efficacy is determined by measuring from the baseline, the: spirometric measurement of forced expiratory volume in one second ($FEV_1$), the spirometric measurements of forced vital capacity (FVC), the acute respiratory illness checklist (ARIC) score, change in health-related quality of life determined from the cystic fibrosis quality of life (CFQOL) questionnaire, cumulative incidence of the use of intravenous (IV) antibiotics, number of hospitalizations and number of days hospitalized, change in computed tomography (CT) imaging. Safety assessment included the ARIC scores, use of IV antibiotics, number of hospitalizations, CT imaging, physical examinations, vital sign measurements, clinical laboratory evaluations, documentations of AEs, and electrocardiogram (ECG) assessments. The total duration of the study is 18 months.

Example 4

Assessing the Safety and Efficacy of Nebulized Anakinra in Subjects with Emphysema A double-blind, randomized, placebo-controlled, multi-center phase II study is performed with 120 subjects diagnosed with emphysema. Ninety (90) subjects receive nebulized inhalation of anakinra and thirty (30) subjects received placebo as control. The subjects are separated into four (4) dose groups. Dosage forms of anakinra are administered as follows: thirty (30) subjects received dosage levels of 0.75 mg, thirty (30) subjects receive dosage levels of 3.75 mg, thirty (30) subjects receive dosage levels of 7.5 mg; the fourth group of thirty (30) subjects, receive placebo as a control. The study medication is administered once daily for 12 months. Drug efficacy is determined by measuring from the baseline, the: time of the first exacerbation and the number of pulmonary exacerbations, change in lung density measured by CT scans, the spirometric measurements of forced vital capacity (FVC), the acute respiratory illness checklist (ARIC) score, cumulative incidence of the use of intravenous (IV) antibiotics, number of hospitalizations and number of days hospitalized and the St. George's respiratory questionnaire which include questions on lung functions ($FEV_1$ and DLCO), body mass index, exercise capacity, mortality, quality of life and safety. The total duration of the study is 18 to 24 months.

Example 5

Content Uniformity

This test is designed to demonstrate the uniformity of medication per spray (or minimum dose), consistent with the label claim, to be discharged from the actuator or mouth piece, of an appropriate number (n=about 10 from beginning and n=about 10 from end) of containers from a batch. The primary purpose is to ensure spray content uniformity within the same container and among multiple containers of a batch.

Techniques for thoroughly analyzing the spray discharged from the actuator or mouth piece for the drug substance content include multiple sprays from beginning to the end of an individual container, among containers, and among batches of drug product. This test provides an overall performance evaluation of a batch, assessing the formulation, the manufacturing process, and the pump. At most, two sprays per determination are used except in the case where the number of sprays per minimum dose specified in the product labeling is one. To ensure reproducible in vitro dose collection, the procedure will have controls for actuation parameters (e.g., stroke length, actuation force). The test is performed with units primed following the instructions in the labeling. The amount of drug substance delivered from the actuator or mouth piece is expressed both as the actual amount and as a percentage of label claim.

The following acceptance criteria are used. However, alternative approaches (e.g., statistical) may be used to provide equal or greater assurance of spray content uniformity.

In general, for acceptance of a batch (1) the amount of active ingredient per determination is not outside of 80 to 120 percent of label claim for more than 2 of 20 determinations (10 from beginning and 10 from end) from 10 containers, (2) none of the determinations is outside of 75 to 125 percent of the label claim, and (3) the mean for each of the beginning and end determinations are not outside of 85 to 115 percent of label claim.

If the above acceptance criteria are not met because 3 to 6 of the 20 determinations are outside of 80 to 120 percent of the label claim, but none are outside of 75 to 125 percent of label claim and the means for each of the beginning and end determinations are not outside of 85 to 115 percent of label claim, an additional 20 containers will be sampled for second-tier testing.

For the second tier of testing of a batch, the acceptance criteria are met if (1) the amount of active ingredient per determination is not outside of 80 to 120 percent of the label claim for more than 6 of all 60 determinations, (2) none of the 60 determinations is outside of 75 to 125 percent of label claim, and (3) the means for each of the beginning and end determinations are not outside of 85 to 115 percent of label claim.

Example 6

Testing Particle Size Distribution

When testing particle size distribution for both suspension and solution aerosols and sprays, an appropriate control is important (e.g., 3 to 4 cut-off values) of the delivered plume subsequent to spraying under specified experimental and instrumental conditions. In this example, a laser diffraction method is used, and droplet size distribution is controlled in terms of ranges for the $D_{10}$, $D_{50}$, $D_{90}$, span $[(D_{90}-D_{10})/D_{50}]$, and percentage of droplets less than 10 micrometers is determined.

A multistage cascade impactor is used to fractionate and collect droplets/particles of the composition formulation by aerodynamic diameter through serial multistage impactions. Such a device with all associated accessories allows determination of a size distribution throughout the whole dose including, in particular, the small particle/droplet size fraction of the dose. It also provides information that allows the complete mass balance of the total labeled dose to be determined. To minimize distortions and to ensure reproducibility, the conditions are stipulated for a specific composition such as the calibration of the equipment, flow rate, duration, size, and shape of the expansion chamber or inlet stem, and the procedure, accessories, and adapter that introduce the inhalation spray into a specified impactor. These important parameters are determined to obtain a complete profile of the dose. Before multiple cascade impactors of the same design are used, data will demonstrate comparability between impactor units.

The aerodynamic particle/droplet size distribution analysis and the mass balance obtained (drug substance deposited on surfaces from the inlet to the cascade impactor filter) are used to determine the suitability of the device with the composition. The total mass of drug collected on all stages, accessories will be monitored on a given composition, and a suitable device will deliver between 85 and 115 percent of label claim on a per spray basis.

Example 7

Spray Pattern and Plume Geometry

The following testing is used to characterize spray pattern and plume geometry when evaluating the performance of the device. Various factors can affect the spray pattern and plume geometry, including the size and shape of the nozzle, the design of the device, the size of the metering chamber, and the characteristics of the formulation. Spray pattern testing is performed on a routine basis as a quality control for release of the drug product. Characterization of plume geometry typically is established during the characterization of the product.

In the evaluation of the spray pattern, the spray distance between the nozzle and the collection surface, number of sprays per spray pattern, position, and orientation of the collection surface relative to the nozzle, and visualization procedure are specified. The acceptance criteria for spray pattern includes the shape (e.g., ellipsoid of relative uniform density) as well as the size of the pattern (e.g., no axis is greater than x millimeters and the ratio of the longest to the shortest axes should lie in a specified range). Data are generated to demonstrate that the collection distance selected for the spray pattern test provide the optimal discriminatory capability. Variability in the test is controlled by the use of a product specific detection procedure.

Plume geometry is evaluated by a variety of procedures (e.g., the time sequence sound-triggered high-speed flash photography method, videotape recording and taking pictures of different frames), all well known in the art. Photographs are of high quality. When monitoring the plume development and to define the shape two views, at 90 degrees to each other and relative to the axis of the plume of the individual spray plume are used.

Example 8

Test of Particle Size Distribution

One form of control that is critical for inhalation aerosols is particle size distribution of the delivered dose. This parameter is dependent on the formulation, the valve, and the mouthpiece. The optimum aerodynamic particle size distribution for most inhalation aerosols has generally been recognized as being in the range of 1-5 microns.

From a pharmaceutical viewpoint, the most important parameter for an inhalation product is usually the aerodynamic particle size distribution of the outgoing aerosol. The aerodynamic particle size distribution is influenced by the characteristics of the spray of the drug product, as well as other factors, and is not solely determined by the size of the individual drug substance particles initially suspended in the formulation.

The quantitative procedure is determined by the specific composition of the invention and validated, if feasible, in terms of its sensitivity and ability to detect shifts that may occur in the distribution.

When examining formulations of the composition containing suspending agents in the presence of suspended drug substance, and the procedure cannot be acceptably validated, a qualitative and semiquantitative method for examination of drug and aggregated drug particle size distribution is used. For example, microscopic evaluation is used and such an examination provides information and data on the presence of large particles, changes in morphology of the drug substance particles, extent of agglomerates, and crystal growth.

Example 9

Test of Particulate Matter

Particulate matter may originate during manufacturing, from formulation components, and from the container and closure components. Levels of particulate matter in the drug product can increase with time, temperature, and stress. If stability data generated in support of the application demonstrate that levels of particulate matter do not increase with time, this testing of this attribute will occur during batch release. In general, the acceptance criteria will include limits for foreign particulate matter less than 10 micrometers, greater than 10 micrometers, and greater than 25 micrometers. For a description of this test, refer to the USP.

Example 10

Test of Microbial Contaminants

The microbial quality is controlled by appropriate methods and checked by microbial testing well known in the art. For a description of this test, refer to the procedure in USP. Acceptance criteria for total aerobic count, total yeast and mold count, and freedom from designated indicator organisms are used. Testing will show that the drug product does not support the growth of microorganisms and that microbiological quality is maintained throughout the expiration dating period.

Example 11

Test of pH

For both solution and suspension sprays, the pH or apparent pH, as appropriate, of the formulation are tested and an appropriate acceptance criterion established. For a description of this test, refer to the USP.

Example 12

Test of Osmolality

For formulations containing an agent to control the tonicity or for products having a label claim regarding tonicity, the osmolality of the formulation should be tested and controlled at release with an appropriate procedure and acceptance criterion. For a description of this test, refer to the USP.

Example 13

Test of Viscosity

For formulations of the composition that contain an agent contributing to the viscosity, this parameter will be tested and controlled at release and on stability with an appropriate procedure and acceptance criterion. For a description of this type of test, refer to the USP.

Example 14

Label for Container

In this illustration, a "label" includes the following information: established name of the drug product, amounts of the drug substance delivered from the inhaler or mouthpiece, number of medication doses per container, net content (fill) weight, usual dosage, excipients (established names), route of administration, recommended storage conditions including any warning statements regarding temperature or light exposure, manufacturer's and/or distributor's name and address, "prescription only" statement, lot number, expiration date, use period once drug product is removed from protective packaging (if applicable), and instructions regarding shaking of suspension drug products, Where the lower airways delivery device for the composition can be reused repeatedly with one or more reservoirs, each reservoir may be labeled separately.

In the case of small labels, only some of the information listed above must be included in the label (21 CFR 201.10 (i)). However, all labeling information required by the Federal Food, Drug, and Cosmetic Act (the Act) and the regulations in Title 21 of the Code of Federal Regulations must be included on the carton, outer container, wrapper, and leaflet as appropriate.

Example 15

Package Insert

The package insert includes the following information that is specific for the delivery device used:

The medication dose delivered to the patient is expressed by a statement, such as each dose delivers (amount mcg) of drug substance in (amount in mg) of suspension or solution equivalent to (amount in mcg) of drug substance base (if applicable) from the actuator or mouthpiece.

For suspension formulations, if the drug substance forms solvates or hydrates, this formation are clearly specified with proper conversion for the active drug shown.

A list of all excipients is included. Substances are identified by their established names.

The number of priming sprays before using the delivery device for the first time is included. The number of priming sprays for a unit that has not been used for more than a specified period is included.

The net content (fill) weight of the container is stated.

The number of medication sprays expected throughout the shelf life of the drug product is indicated for each container fill weight.

The color and appearance of the container, closure, and inhaler components is included.

A statement is provided that the correct amount of medication in each inhalation cannot be ensured after the labeled number of doses from the unit even though the unit may not be completely empty. In addition, for reusable devices with replacement cartridges or refill units, a statement is included that these units should be discarded when the labeled numbers of inhalations have been dispensed and this labeling is applied to these units, not the device. The device is labeled with an appropriate replacement or service interval. Storage conditions are clearly stated including any warning statements regarding temperature and light exposure. Any preferred storage orientation is also indicated. In certain cases when a protective packaging (e.g., foil overwrap) is warranted to ensure product quality and is used for the drug product, this is clearly stated. In addition, when appropriate and where the contents of the protective packaging should not be used after a specified number of days (e.g., 2 weeks, 30 days) from the date the protective packaging was removed, this is clearly stated. A statement is included regarding recommendations for shaking, if warranted (i.e., for suspension products).

Example 16

Instructions for Use

The instructions to the patient include the following if applicable:

Detailed, step-by-step, set of appropriately illustrated instructions for patient use is included. Figures include the various elements of the container closure system. Instructions for initial priming and for repriming of the unit are also included where appropriate. Also included is a statement cautioning against contact with the eyes, where appropriate. Storage conditions are clearly stated, including any warning statements regarding temperature and light exposure. A statement is included regarding recommendations for shaking, if warranted (i.e., for suspension products). Any preferred storage orientation should be noted. Where protective packaging is used for the drug product, appropriate statements are included that the contents of the protective packaging should not be used after a specified number of days (e.g., 2 weeks, 30 days) from the date the protective packaging was removed. Appropriate cleaning instructions are also included (if applicable). Finally, a statement is included that the correct amount of medication in each spray cannot be ensured after the labeled number of sprays even if there is evidence that the unit is not completely empty. This statement also instructs the patient to keep track of the number of sprays used from the container unless a counter mechanism is incorporated into the device.

Example 17

Therapeutic Effects of a Proinflammatory Cytokine Inhibitor on Nonallergic Lower Airways Inflammation The following example illustrates methods for assessing the therapeutic effects of a proinflammatory cytokine inhibitor on nonallergic lower airways inflammation.

An exploratory single-center, double blind, placebo-controlled, randomized, phase 2 trial is performed with 30 active smokers with mild-to-moderate chronic obstructive pulmonary disease. Twenty patients received daily oral nebulized inhalation of infliximab (5 mg) for 60 days, and ten patients received oral nebulized saline daily.

COPD is identified by history, clinical symptoms, and laboratory findings including abnormal PFTs, exercise capacity, and validated questionnaire. Sputum samples, respiratory symptoms, quality of life, exhaled nitric oxide, lung function parameters, bronchial hyperresponsiveness, resting energy expenditure, and side effects were evaluated. Allergic predisposition is assessed by skin-prick tests performed with a standard panel of 10 or more common airborne allergens (ALK, Copenhagen, Denmark) including pollen, house dust mites, mold, and animal allergens. All subjects with a positive skin for at least one allergen are considered allergic and separated from nonallergic subjects during study. Steroids are withheld for a minimum of 6 weeks prior to the study. All studies are approved by the Institutional Review Board or Ethics Committee as needed and an informed written consent is obtained from each subject.

Quantification of eosinophil and neutrophil numbers in sputum is performed by counting numbers of human neutrophil elastase (HNE)-stained (for neutrophils) and EG2-stained (for eosinophils) cells in a defined area of a defined volume of aspirate. Results are expressed as the average number of cells per volume of lavage fluid.

Quantification of cytokines is performed using commercially available ELISA methods as per the suppliers' instructions. All results are normalized for a normal BAL protein/serum protein.

Data obtained before and after test article and control treatments are compared using the nonparametric Wilcoxon signed-rank test. A p-value<0.05 for the null hypothesis was accepted as indicating a statistically significant difference.

Generally, subjects treated with test article are expected to show a significant improvement in lung functions, symptom scores, exercise capacity and reduced BAL inflammatory cells relative to baseline and control treatment.

Example 18

Determination of Appropriate Storage Conditions

These studies assess formulation and container and closure system, and the necessity for secondary or additional protective packaging. The following changes are considered significant:

A 5 percent change from the initial drug content assay value of a batch;

A failure to meet established stability acceptance criteria except for dose content uniformity and particle size distribution criteria;

For dose content uniformity, a 10 percent change in the mass of the mean dose (beginning, middle, and end means determined separately) at any test interval relative to the initial time-point value or failure to meet the established acceptance criteria for the first tier of testing.

For particle size distribution, generally a greater than 10 percent change in the total mass of relevant fine particles (e.g., particles less than 5 micrometers) within the particle size distribution or a shift in the profile for these particles.

Initially, the drug product without protective or secondary packaging (e.g., MDI canister, blister units, device-metered DPIs) and in certain cases without primary packaging (e.g., capsules for DPIs) are stored under accelerated conditions of (40° C./75% RH) and tested for all stability parameters at the appropriate test intervals.

Example 19

Stability of Primary (Unprotected) Package

When a secondary or additional protective packaging (e.g., foil overwrap) is deemed necessary for a particular composition and drug product, adequate stability data from a study conducted at a minimum of 25° C. and 75% RH are generated on these units without the protective package to establish the maximum acceptable length of time is appropriate for patient use after the protective packaging is removed. Drug products both newly manufactured and near the end of the proposed expiration-dating period are evaluated.

Example 20

Temperature Cycling

For MDI inhalation aerosols, a stress temperature cyclic study is performed on the effects of temperature and associated humidity changes on the quality and performance of the drug product, under extremes of high and low temperatures that may be encountered during shipping and handling. The study consists of three or four six-hour cycles per day, between subfreezing temperature and 40/C for a period of up to six weeks. At the end of predetermined cycles, the samples are analyzed for appropriate parameters and compared with the control drug product. Analyses for MDIs after cycling studies include particle size distribution, microscopic evaluation, physical appearance of the content, valve component integrity, dose content uniformity, water content, and leak rate. MDI drug product appearance is examined for discoloration of the contents, microscopic evaluation, distortion or elongation of valve components, valve clogging, canister corrosion, and adherence of the drug to the walls of the container or valve components.

Example 21

Effect of Resting Time

A study is conducted to determine the effect of increasing resting time on the first actuation of unprimed MDI units followed immediately by the second and the third actuations. MDI units are only primed prior to initiation of the study. After resting for increasing periods of time (e.g., 6, 12, 24, 48 hours), content uniformity of the first, second, and third actuations (no priming) is be determined to define the medication profile per actuation. Testing is performed on MDI containers that have been stored in different orientations (i.e., upright, inverted and/or horizontal.

Example 22

Priming/Repriming

Studies are performed to characterize the drug product in terms of initial priming and repriming requirements after various periods of non-use. The interval that may pass before the MDI needs to be reprimed to deliver the labeled amount of medication should be determined, as well as the number of actuations needed to prime or reprime the MDI.

Example 23

Effect of Storage on the Particle Size Distribution

During primary stability studies for suspension aerosols, the effect of storage on particle size distribution from the initial actuation to the labeled number of actuations is evaluated to determine any trends.

Example 24

Drug Deposition on Mouthpiece and/or Accessories

The amount of drug deposited per actuation on the mouthpiece and any other drug product accessory is measured and documented.

Example 25

Cleaning Instructions

In-use studies are performed to determine the frequency of cleaning and related instructions to be included in the labeling.

Example 26

Profiling of Actuations Near Canister Exhaustion

A study is conducted to determine the profiles of the delivered amount and the aerodynamic particle size distribution of the drug substance of each individual actuation after the point at which the labeled number of actuations have been dispensed until no more actuations are available.

Example 27

Effect of Varying Flow Rates

A study is run to determine the emitted dose and the particle size distribution as a function of different flow rates at constant volume. The total volume is limited to two liters. This study assesses the sensitivity of the device to widely varying flow rates that will be generated by patients of different ages and gender and with different severity of disease. To examine the effects of severe limitations of a patient's forced expiratory volume in one second ($FEV_1$) on inspiratory flow rates that can be generated through the device, stable, severe COPD subjects are used.

Example 28

Fill Weight

For device-metered DPIs, the optimum and minimum fill weight for a given reservoir size and geometry is determined and documented to justify the proposed overfill and to ensure consistent dose content uniformity and particle size distribution through the labeled number of doses from the device under use conditions.

Example 29

Device Ruggedness

For pre-metered DPIs that may be reused repeatedly, a study is conducted to establish the DPI's performance characteristics (emitted dose and particle size distribution) throughout the life of the device.

Example 30

Therapeutic Effects of a Proinflammatory Cytokine Inhibitor on Nonallergic Lower Airways Inflammation The following example illustrates methods for assessing the therapeutic effects of a proinflammatory cytokine inhibitor on nonallergic lower airways inflammation.

An exploratory single-center, double blind, placebo-controlled, randomized, phase 2 trial is performed with 120 active smokers with mild-to-moderate chronic obstructive pulmonary disease. Thirty patients receive daily oral nebulized inhalation of adalimumab (5 mg) for 120 days; another thirty patients receive daily oral nebulized inhalation of adalimumab (5 mg) for 106 days following one subcutaneous injection of adalimumab (40 mg) 14 days earlier; another thirty patients receive daily oral nebulized inhalation of adalimumab (5 mg) for 92 days following two subcutaneous injections of adalimumab (40 mg) 28 days earlier, and a fourth group of thirty patients receive oral nebulized saline daily for 120 days.

COPD is identified by history, clinical symptoms, and laboratory findings including abnormal PFTs, exercise capacity, and validated questionnaire. Sputum samples, respiratory symptoms, quality of life, exhaled nitric oxide, lung function parameters, bronchial hyperresponsiveness, resting energy expenditure, and side effects were evaluated. Allergic predisposition is assessed by skin-prick tests performed with a standard panel of 10 or more common airborne allergens (ALK, Copenhagen, Denmark) including pollen, house dust mites, mold, and animal allergens. All subjects with a positive skin for at least one allergen are considered allergic and separated from nonallergic subjects during study. Steroids are withheld for a minimum of 6 weeks prior to the study. All studies are approved by the Institutional Review Board or Ethics Committee as needed and an informed written consent is obtained from each subject.

Quantification of eosinophil and neutrophil numbers in sputum is performed by counting numbers of human neutrophil elastase (HNE)-stained (for neutrophils) and EG2-stained (for eosinophils) cells in a defined area of a defined volume of aspirate. Results are expressed as the average number of cells per volume of lavage fluid.

Quantification of cytokines is performed using commercially available ELISA methods as per the suppliers' instructions. All results are normalized for a normal BAL protein/serum protein.

Data obtained before and after test article and control treatments are compared using the nonparametric Wilcoxon signed-rank test. A p-value<0.05 for the null hypothesis was accepted as indicating a statistically significant difference.

Generally, subjects treated with test article are expected to show a significant improvement in lung functions, symptom scores, exercise capacity and reduced BAL inflammatory cells relative to baseline and control treatment.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled. All cited patents, patent applications, and publications referred to in this application are herein incorporated by reference in their entirety.

What is claimed:

1. A method for treating an inflammatory disorder of lower airways in a human subject in need thereof, the method comprising administering directly to the lower airways in the human subject an effective amount of anakinra, wherein the effective amount of anakinra is administered using a nebulizer.

2. The method of claim 1, wherein the effective amount of anakinra is between 0.01 mg and 100 mg per day.

3. The method of claim 1, wherein the inflammatory disorder of the lower airways is selected from the group consisting of acute bronchitis, chronic bronchitis, bronchiolitis, emphysema, Still's disease, Wegener's disease, Behcet's disease, keratoscleritis, lymphomatous tracheobronchitis, Cogan's syndrome, chronic obstructive pulmonary disease, cystic fibrosis, bronchiolitis obliterans syndrome, allograft rejection, lung injury, and a combination thereof.

4. The method of claim 3, wherein the inflammatory disorder of the lower airways is acute bronchitis.

5. The method of claim 3, wherein the inflammatory disorder of the lower airways is chronic bronchitis.

6. The method of claim 3, wherein the inflammatory disorder of the lower airways is bronchiolitis.

7. The method of claim 3, wherein the inflammatory disorder of the lower airways is emphysema.

8. The method of claim 3, wherein the inflammatory disorder of the lower airways is Still's disease.

9. The method of claim 3, wherein the inflammatory disorder of the lower airways is Wegener's disease.

10. The method of claim 3, wherein the inflammatory disorder of the lower airways is Behcet's disease.

11. The method of claim 3, wherein the inflammatory disorder of the lower airways is keratoscleritis.

12. The method of claim 3, wherein the inflammatory disorder of the lower airways is lymphomatous tracheobronchitis.

13. The method of claim 3, wherein the inflammatory disorder of the lower airways is Cogan's syndrome.

14. The method of claim 3, wherein the inflammatory disorder of the lower airways is chronic obstructive pulmonary disease.

15. The method of claim 3, wherein the inflammatory disorder of the lower airways is cystic fibrosis.

16. The method of claim 3, wherein the inflammatory disorder of the lower airways is bronchiolitis obliterans syndrome.

17. The method of claim 3, wherein the inflammatory disorder of the lower airways is allograft rejection.

18. The method of claim 3, wherein the inflammatory disorder of the lower airways is lung injury.

19. The method of claim 1, wherein the inflammatory disorder of the lower airways is associated with a bacterial infection in the human subject.

20. The method of claim 1, wherein the inflammatory disorder of the lower airways is associated with a viral infection in the human subject.

21. The method of claim 1, wherein the nebulizer releases a mixture comprising anakinra, wherein the mixture comprises a plurality of particles, and wherein the plurality of particles comprises an average particle size of less than 20 microns in diameter.

22. The method of claim 21, wherein the plurality of particles comprises an average particle size of less than 10 microns in diameter.

23. The method of claim 22, wherein the plurality of particles comprises an average particle size of less than 5 microns in diameter.

24. The method of claim 23, wherein the plurality of particles comprises an average particle size of between 1 micron and 5 microns in diameter.

25. The method of claim 24, wherein the plurality of particles comprises an average particle size of between 3 microns and 5 microns in diameter.

26. The method of claim 1, further comprising administering two or more doses of anakinra in less than 5 minutes apart.

\* \* \* \* \*